United States Patent
Jin et al.

(10) Patent No.: US 12,037,642 B2
(45) Date of Patent: Jul. 16, 2024

(54) HELIX 73-DERIVED RNA MOLECULES INTERACTING WITH ERM PROTEIN AND METHODS OF USING THE SAME

(71) Applicant: INDUSTRY-UNIVERSITY COOPERATION OF USW, Hwaseong-si (KR)

(72) Inventors: Hyung Jong Jin, Seoul (KR); Hak Jin Lee, Seoul (KR)

(73) Assignee: INDUSTRY-UNIVERSITY COOPERATION OF USW, Gyeonggi-Do (KR)

( * ) Notice: Subject to any disclaimer, the term of this patent is extended or adjusted under 35 U.S.C. 154(b) by 140 days.

(21) Appl. No.: 17/410,504

(22) Filed: Aug. 24, 2021

(65) Prior Publication Data

US 2022/0056524 A1 Feb. 24, 2022

(30) Foreign Application Priority Data

Aug. 24, 2020 (KR) ........................ 10-2020-0106533

(51) Int. Cl.
*C07H 21/02* (2006.01)
*C12Q 1/6876* (2018.01)

(52) U.S. Cl.
CPC ........... *C12Q 1/6876* (2013.01); *C07H 21/02* (2013.01); *C12Q 2600/154* (2013.01); *C12Q 2600/158* (2013.01)

(58) Field of Classification Search
CPC .................. C12Q 2600/154; C12Q 1/6876
See application file for complete search history.

(56) References Cited

PUBLICATIONS

Sharkey et al. (RNA, 2022, 28, 210-226).*
Berryman et al. (Antimicrobial Agents and Chemotherapy, 1995, 1830-1834, 39, 8).*
McClatchey (Journal of Cell Science, 2014, 127, 3199-3204).*
Hyung Jong Jin; Role of stem74 in substrate activity which is composed of stem 73 and 74 for ErmS; Creative Commons Common Deed; ISSN 1225-6668; 2019.

Le, Tien et al.; "Recognition Site Generated by Natural Changes in Erm Proteins Leads to Unexpectedly High Susceptibility to Chymotrypsin" ACS Omega 2017, 2, 8129-8140; Nov. 20, 2017 http://pubs.acs.org/journal/acsodt.
Macrina, Francis et al; "A cloning vector able to replicate in *Escherichia coli* and *Streptococcus sanguis*;" Gene, 19 (1982) 345-353 Elsevier Biomedical Press.
Wilson, Vanessa T.W. et al. Molecular Analysis of tlrB, an Antibiotic-resistance Gene from Tylosin-producing Streptomyces fradiae, and Discovery of a Novel Resistance Mechanism; vol. 52, No. 3, Mar. 1999 the Journal of Antibiotics pp. 288-296.
Lee HJ, Park YI, Jin HJ. 2020. Plausible minimal substrate for Erm protein. Antimicrob Agents Chemother 64: e00023-20. https://doi.org/10.1128/AAC.00023-20.
Ae Kyung Park, Ho Kim, Hyung Jong Jin, Phylogenetic analysis of rRNA methyltransferases, Erm and KsgA, as related to antibiotic resistance, FEMS Microbiology Letters, vol. 309, Issue 2, Aug. 2010, pp. 151-162, https://doi.org/10.1111/j.1574-6968.2010.02031.x.
Wilson VT, Cundliffe E. 1999. Molecular analysis of tlrB, an antibiotic-resistance gene from tylosin-producing Streptomyces fradiae, and discovery of a novel resistance mechanism. J Antibiot (Tokyo) 52:288-296].
Kovalic D, Giannattasio RB, Jin HJ, Weisblum B. 1994. 23S rRNA domain V, a fragment that can be specifically methylated in vitro by the ErmSF (TlrA) methyltransferase. J Bacteriol 176:6992-6998.
Zhong P, Pratt SD, Edalji RP, Walter KA, Holzman TF, Shivakumar AG, Katz L. 1995. Substrate requirements for ErmC= methyltransferase activity. J Bacteriol 177:4327-4332.
Jin HJ, Yang YD. 2002.; Purification and biochemical characterization of the ErmSF macrolide-lincosamide-streptogramin B resistance factor protein expressed as a hexahistidine-tagged protein in *Escherichia coli*. Protein Expr Purif 25:149-159.
Zalacain M, Cundliffe E. 1989. [Methylation of 23S rRNA caused by tlrA (ermSF), a tylosin resistance determinant from Streptomyces fradiae. J Bacteriol 171:4254-4260.

* cited by examiner

*Primary Examiner* — Amy Rose Hudson
(74) *Attorney, Agent, or Firm* — D'Ambrosio & Menon, PLLC; Usha Menon

(57) ABSTRACT

The RNA molecule of the present invention, which is based on a helix 73-derived RNA substrate and Erm interaction sites, may be used for screening candidate substances that inhibit methylation by Erm, developing variants thereof, and identifying the action mechanism, and may be used for suppressing the expression of antibiotic resistance.

8 Claims, 13 Drawing Sheets

Specification includes a Sequence Listing.

Domain V

MS

HELIX 73-DERIVED RNA MOLECULES INTERACTING WITH ERM PROTEIN AND METHODS OF USING THE SAME

CROSS-REFERENCE TO RELATED APPLICATIONS

This application is related to and claims priority to Korean Patent Application No. 10-2020-0106533, filed on Aug. 24, 2020, the contents of which are incorporated by reference herein in its entirety.

INCORPORATION BY REFERENCE

This application includes a sequence listing in computer readable form (a "txt" file) that is submitted herewith on ASCII text file named PX065830ST25_rev.txt, created on Oct. 14, 2021 and 13,824 bytes in size. This sequence listing is incorporated by reference herein.

BACKGROUND

1. Field

The present invention relates to helix 73-derived RNA molecules interacting with Erm proteins and uses thereof.

2. Description of the Related Art

Antibiotic resistance refers to the ability of bacteria to survive or proliferate without being affected by antibiotics. New antibiotics for use in combatting antibiotic-resistant bacteria have been developed, but bacteria can also easily obtain resistance to the new antibiotics. Therefore, it is required and important to suppress the expression of antibiotic resistance by bacteria in the development and use of antibiotics.

Erythromycin resistance methylase (Erm) has been known to be involved in the process by which bacteria acquire resistance to macrolide-lincosamide-streptogramin B ($MLS_B$) antibiotics. Therefore, inhibition of Erm is expected to suppress the acquisition of antibiotic resistance by bacteria, and furthermore, to eliminate the acquired resistance. Despite studies on Erm activities so far, the action mechanism thereof has not yet been clearly elucidated, and an efficient method for screening Erm inhibitors is yet to be established.

SUMMARY

According to one aspect, provided are an RNA molecule derived from Helix 73 that interacts with an Erm protein and a method of using same.

Additional aspects will be set forth in part in the description which follows and, in part, will be apparent from the description, or may be learned by practice of the presented embodiments of the disclosure.

In one aspect, provided is a double-stranded RNA molecule which is methylated by the Erm protein, in which a first strand consisting of the sequence of SEQ ID NO: 1 and a second strand consisting of the sequence of SEQ ID NO: 2 are paired while forming 13 base pairs, the first and second bases of SEQ ID NO: 1 form a 5' overhang, the 19th to 22nd bases of SEQ ID NO: 1 form a 3' overhang, and the 11th base of SEQ ID NO: 1 is an unpaired base.

According to an embodiment, the double-stranded RNA molecule may include: a first Erm interaction site consisting of 3 base pairs between 3rd to 5th bases of SEQ ID NO: 1 and the bases complementary thereto; a second Erm interaction site consisting of 5 base pairs between 6th to 10th bases of SEQ ID NO: 1 and the bases complementary thereto; a minimum substrate site; and a third Erm interaction site consisting of 19th to 22nd bases of SEQ ID NO: 1.

It was found that the double-stranded RNA molecule serves as a substrate for methylation by the Erm protein. The sequences including those of SEQ ID NO: 1 and SEQ ID NO: 2 are shown in Table 1 below.

TABLE 1

| Seq ID | name | sequence (5' -> 3') |
|---|---|---|
| 1 | First strand | GGCCC GCGAC AGGAC GGAAA GA |
| 2 | Second strand | CCUAU CCGUC GCGGG |
| 3 | Tetraloop | UUCG |
| 4 | Tetraloop | GCAA |
| 5 | Hairpin loop | AAAGA CC |
| 6 | Sense sequence of First Erm interaction site | CCC |
| 7 | Sense sequence of Second Erm interaction site | GCGAC |
| 8 | Sense sequence of First and Second Erm interaction sites | CCCGC GAC |
| 9 | Sense sequence of Minimum substrate site | AGGAC GGA |
| 10 | Antisense sequence of Minimum substrate site | CCUAU CC |

TABLE 1-continued

| Seq ID | name | sequence (5' -> 3') |
|---|---|---|
| 11 | Sense sequence of Second Erm interaction site + Minimum substrate site | GCGAC AGGAC GGA |
| 12 | Antisense sequence of Second Erm interaction site + Minimum substrate site | CCUAU CCGUC GC |
| 13 | Sense sequence of Minimum substrate site + Third Erm interaction site | AGGAC GGAAA GA |
| 14 | Antisense sequence of Minimum substrate site + Third Erm interaction site | CCUAU CC |
| 15 | Sense sequence of First Erm interaction site + Second Erm interaction site + Minimum substrate site | CCCGC GACAG GACGG A |
| 16 | Antisense sequence of First Erm interaction site + Second Erm interaction site + Minimum substrate site | CCUAU CCGUC GCGGG |
| 17 | Sense sequence of Second Erm interaction site + Minimum substrate site + Third Erm interaction site | GCGAC AGGAC GGAAA GA |
| 18 | Antisense sequence of Second Erm interaction site + Minimum substrate site + Third Erm interaction site | CCUAU CCGUC GC |
| 61 | 23S rRNA Domain V fragment 583nt (*Bacillus subtilis* 2072-2654: on the basis of *Bacillus subtilis* Accession no NR_103037) | <u>CCCGCGACAG GACGGAAAGA</u> CCCCGUGGAG CUUUACUGCA GCCUGAUAUU GAAUGUUGGU ACAGCUUGUA CAGGAUAGGU AGGAGCCUUG GAAACCGGAG CGCCAGCUUC GGUGGAGGCA UCGGUGGGAU ACUACCCUGG CUGUAUUGAC CUUCUAACCC GCCGCCCUUA UCGGGCGGGG AGACAGUGUC AGGUGGGCAG UUUGACUGGG GCGGUCGCCU CCUAAAAGGU AACGGAGGCG CCCAAAGGUU CCCUCAGAAU GGUUGGAAAU CAUUCGCAGA GUGUAAAGGC ACAAGGGAGC UUGACUGCGA GACCUACAAG UCGAGCAGGG ACGAAAGUCG GGCUUAGUGA UCCGGUGGUU CCGCAUGGAA GGGCCAUCGC UCAACGGAUA AAAGCUACCC CGGGGAUAAC AGGCUUAUCU CCCCCAAGAG UCCACAUCGA CGGGGAGGUU UGGCACCUCG AUGUCGGCUC AUCGCAUCCU GGGGCUGUAG UCGGUCCCAA GGGUUGGGCU GUUCGCCCAU UAAAGCGGUA CGCGAGCUGG GUUCAGAACG UCGUGAGACA GUUCGGUC<u>CC UAUCCGUCGC GGG</u> |
| 62 | 577nt | GCGACAGGAC GGAAAGACCC CGUGGAGCUU UACUGCAGCC UGAUAUUGAA UGUUGGUACA GCUUGUACAG GAUAGGUAGG AGCCUUGGAA ACCGGAGCGC CAGCUUCGGU GGAGGCAUCG GUGGGAUACU ACCCUGGCUG UAUUGACCUU CUAACCCGCC GCCCUUAUCG GGCGGGGAGA CAGUGUCAGG UGGGCAGUUU GACUGGGGCG GUCGCCUCCU AAAAGGUAAC GGAGGCGCCC AAAGGUUCCC UCAGAAUGGU UGGAAAUCAU UCGCAGAGUG UAAAGGCACA AGGGAGCUUG |

TABLE 1-continued

| Seq ID | name | sequence (5' -> 3') |
|---|---|---|
| | | ACUGCGAGAC CUACAAGUCG |
| | | AGCAGGGACG AAAGUCGGGC |
| | | UUAGUGAUCC GGUGGUUCCG |
| | | CAUGGAAGGG CCAUCGCUCA |
| | | ACGGAUAAAA GCUACCCCGG |
| | | GGAUAACAGG CUUAUCUCCC |
| | | CCAAGAGUCC ACAUCGACGG |
| | | GGAGGUUUGG CACCUCGAUG |
| | | UCGGCUCAUC GCAUCCUGGG |
| | | GCUGUAGUCG GUCCCAAGGG |
| | | UUGGGCUGUU CGCCCAUUAA |
| | | AGCGGUACGC GAGCUGGGUU |
| | | CAGAACGUCG UGAGACAGUU |
| | | CGGUCCCUAU CCGUCGC |
| 63 | 567nt | AGGACGGAAA GACCCCGUGG |
| | | AGCUUUACUG CAGCCUGAUA |
| | | UUGAAUGUUG GUACAGCUUG |
| | | UACAGGAUAG GUAGGAGCCU |
| | | UGGAAACCGG AGCGCCAGCU |
| | | UCGGUGGAGG CAUCGGUGGG |
| | | AUACUACCCU GGCUGUAUUG |
| | | ACCUUCUAAC CCGCCGCCCU |
| | | UAUCGGGCGG GGAGACAGUG |
| | | UCAGGUGGGC AGUUUGACUG |
| | | GGGCGGUCGC CUCCUAAAAG |
| | | GUAACGGAGG CGCCCAAAGG |
| | | UUCCCUCAGA AUGGUUGGAA |
| | | AUCAUUCGCA GAGUGUAAAG |
| | | GCACAAGGGA GCUUGACUGC |
| | | GAGACCUACA AGUCGAGCAG |
| | | GGACGAAAGU CGGGCUUAGU |
| | | GAUCCGGUGG UUCCGCAUGG |
| | | AAGGGCCAUC GCUCAACGGA |
| | | UAAAAGCUAC CCCGGGGAUA |
| | | ACAGGCUUAU CUCCCCCAAG |
| | | AGUCCACAUC GACGGGGAGG |
| | | UUUGGCACCU CGAUGUCGGC |
| | | UCAUCGCAUC CUGGGGCUGU |
| | | AGUCGGUCCC AAGGGUUGGG |
| | | CUGUUCGCCC AUUAAAGCGG |
| | | UACGCGAGCU GGGUUCAGAA |
| | | CGUCGUGAGA CAGUUCGGUC |
| | | CCUAUCC |

Referring to Table 1 and FIG. 1, the first Erm interaction site includes 3 base pairs in which CCC and GGG are complementarily paired, the second Erm interaction site includes 5 base pairs in which GCGAC and GUCGC are complementarily paired, the minimum substrate site is a site where AGGACGG and CCUAUCC are complementarily paired with an internal loop, and the third Erm interaction site is the AAAGA sequence of the first strand. It was found that when at least one of the first Erm interaction site, the second Erm interaction site, and the third Erm interaction site were deleted, substrate methylation by Erm was significantly reduced or eliminated. This is considered to be because the Erm interaction sites affect the binding, allosteric effect or cooperativity of Erm and substrate. In addition, the minimum substrate site refers to the smallest of a substrate required to be methylated by Erm.

The Erm protein methylates a specific adenine residue belonging to domain V of 23S rRNA of various bacteria, thereby conferring resistance to macrolide-lincosamide-streptogramin B (MLSB) antibiotics. The methylated adenine is A2058 on the basis of the 23S rRNA sequence of *E. coli*.

As used herein, the term "overhang" refers to a single-stranded site overhanging from the end of a double-stranded nucleotide sequence without forming base pairs in a double-stranded nucleic acid fragment.

As used herein, the term "unpaired base" refers to a base that does not form a base pair in a double-stranded nucleic acid fragment.

As used herein, the term "Helix 73" refers to the 73rd helix in the secondary structure of 23S rRNA, and refers to a helix formed via base-pairing between starting bases and ending bases of domain V. The domain V and the location of helix 73 are shown in FIG. 2.

As used herein, the term "minimum substrate site" refers to a site or part of a substrate essentially required for methylation by Erm.

As used herein, the term "Erm interaction site" refers to a site or region of a double-stranded RNA substrate that has been identified to interact with Erm for methylation by Erm.

As used herein, the term "antibiotic resistance expression inhibitor" refers to a substance that inhibits antibiotic resistance, and is used interchangeably with an antibiotic resistance inhibitor.

According to an embodiment, in the minimum substrate region, the 12th to 14th bases of SEQ ID NO: 1 and the 5th to 7th bases of SEQ ID NO: 2 are complementarily paired, and the 16th to 17th bases of SEQ ID NO: 1 and the first and second bases of SEQ ID NO: 2 may be complementarily paired (see FIG. 1).

According to an embodiment, the site methylated by the Erm protein in the double-stranded RNA molecule may be the 18th adenine of SEQ ID NO: 1.

Another aspect provides a double-stranded RNA molecule variant containing one or more of the following mutations (a) to (i) in the double-stranded RNA molecule:
(a) deletion of all or part of 5' overhang of the first strand;
(b) truncation of all or part of base pairs between the 5' end of the first strand and the 11th unpaired base of SEQ ID NO: 1;
(c) truncation of all or part of base pairs between the 5' end of the first strand and the 11th unpaired base of SEQ ID NO: 1 and deletion of the first and second bases of SEQ ID NO: 1;
(d) truncation of all or part of base pairs between the 5' end of the first strand and the 11th unpaired base of SEQ ID NO: 1 and addition of a tetraloop sequence to cap the remaining end of the base pairs after truncation;
(e) truncation of all or part of base pairs between the 5' end of the first strand and the 11th unpaired base of SEQ ID NO: 1, addition of a tetraloop sequence to the truncated end of the base pair, and deletion of the first and second bases of SEQ ID NO: 1;
(f) truncation of part of base pairs between the 5' end of the first strand and the 11th unpaired base of SEQ ID NO: 1 and $11^{th}$ unpaired base, addition of a tetraloop sequence to the side of the truncation;
(g) addition of a tetraloop sequence linked to all of base pairs between the 5' end of the first strand and the 11th unpaired base of SEQ ID NO: 1;
(h) addition of a tetraloop sequence linked to all of base pairs between the 5' end of the first strand and the 11th unpaired base of SEQ ID NO: 1 and truncation of the $11^{th}$ unpaired base, and deletion of the first and second bases of SEQ ID NO: 1;

(i) deletion of all or part of 3' overhang of the first strand; and (j) addition of a hairpin loop formed by linking the 3' overhang of the first strand to the 5' end of the second strand which could contain additional nucleotides such as CC.

In (b), the hairpin loop may have a 3' overhang of the first strand linked to the 5' end of the second strand via 2 cytosines.

According to an embodiment, the double-stranded RNA molecule variant may further comprise any one of (a) deletion of all or part of 3 base pairs of the first Erm interaction site; (b) deletion of all of the first Erm interaction site, and deletion of all or part of 5 base pairs of the second Erm interaction site; and (c) deletion of part or all of the first Erm interaction site; all of the first Erm interaction site and part or all of the second Erm interaction site, and addition of a tetraloop. Specifically, in (c), the double-stranded RNA molecule variant may have the tetraloop which connects the 5' end of the remaining first strand and the 3' end of the remaining second strand after part or all of the first Erm interaction site, or all of the first Erm interaction site and part or all of the second Erm interaction site were truncated.

According to an embodiment, the tetraloop sequence may consist of 4 bases, for example, the sequence of SEQ ID NO: 3 or SEQ ID NO: 4, or any sequence capable of increasing the Erm activity may be used, but not limited thereto. The present inventors found that the Erm methylation activity increased by adding the tetraloop sequence consisting of the sequence of SEQ ID NO: 3 or SEQ ID NO: 4.

Further, 577nt obtained by truncating 3 base pairs of the first Erm interaction site from gg583nt was found to retain a considerable level of activity for the Erm protein. In addition, 567nt, in which all 8 base pairs of the first Erm interaction site and the second Erm interaction site were truncated from gg583 nt, did not completely but significantly lose activity for ErmS and ErmE, but totally lost activity for ErmB. In addition, 20nt-I in which both the first and second Erm interaction sites are truncated, had significantly reduced substrate activity for ErmE and ErmS, and lost methylation activity by ErmB. However, 24nt in which the truncated site was capped with a tetraloop sequence showed increase in methylation activity with all of the Erms, and the methylation activity of this substrate using ErmB was 1.3 times higher than that of gg37nt containing all of the first to third Erm interaction sites.

In an embodiment, the double-stranded RNA molecule variant may include deletion of one or more bases from the 3' end of the third Erm interaction site. ErmE and ErmB lost their activity even when only one base of the third Erm interaction site was deleted, but ErmS maintained its activity until the target adenine was present alone. The mutation of the third Erm interaction site may be combined with the mutation of the first Erm interaction site and/or the second Erm interaction site.

According to an embodiment, the double-stranded RNA molecule variant may include a hairpin loop formed by linking the 3' end of the first strand in the third Erm interaction site to the 5' end of the second strand via 2 cytosines (C). The Erm proteins also were found to have methylation activity for gg37nt equipped with a hairpin loop. The hairpin loop may consist of 7 to 8 bases.

According to an embodiment, the double-stranded RNA molecule variant may be the variant modified by combining the mutations of the first Erm interaction site and/or the second Erm interaction site, and/or the mutation of the third Erm interaction site/addition of a hairpin loop.

According to an embodiment, the double-stranded RNA molecule variant may be selected from:

(a) a double-stranded RNA molecule consisting of 3 base pairs in which the sequence of SEQ ID NO: 6 and a sequence complementary thereto are paired, or part thereof, (b) a double-stranded RNA molecule consisting of 5 base pairs in which the sequence of SEQ ID NO: 7 and a sequence complementary thereto are paired, or part thereof, (c) a double-stranded RNA molecule consisting of 8 base pairs in which the sequence of SEQ ID NO: 8 and a sequence complementary thereto are paired, or part thereof, (d) a double-stranded RNA molecule in which the sequence of SEQ ID NO: 9 and the sequence of SEQ ID NO: 10 are paired, or a variant thereof in which a portion of the double stranded RNA molecule is deleted;

(e) a single-stranded RNA molecule consisting of a sequence of SEQ ID NO: 5 in which the 6th and 7th bases are removed, or a partial sequence thereof, (f) a double-stranded RNA molecule in which the sequence of SEQ ID NO: 11 and the sequence of SEQ ID NO: 12 are paired, or a variant thereof in which a portion of the double stranded RNA molecule is deleted;

(g) a double-stranded RNA molecule in which the sequence of SEQ ID NO: 13 and the sequence of SEQ ID NO: 14 are paired, or a variant thereof in which a portion of the double stranded RNA molecule is deleted;

(h) a double-stranded RNA molecule in which the sequence of SEQ ID NO: 1 and the sequence of SEQ ID NO: 2 are paired, or a variant thereof in which a portion of the double stranded RNA molecule is deleted;
(i) a double-stranded RNA molecule in which the sequence of SEQ ID NO: 15 and the sequence of SEQ ID NO: 16 are paired, or a variant in which a portion of the double stranded RNA molecule is deleted; and
(j) a double-stranded RNA molecule in which the sequence of SEQ ID NO: 17 and the sequence of SEQ ID NO: 18 are paired, or a variant thereof in which a portion of the double stranded RNA molecule is deleted.

Another aspect provides a double-stranded RNA molecule to be methylated by an Erm protein, the double-stranded RNA molecule consisting of the sequence of SEQ ID NO: 61, and having a stem structure comprising 13 base pairs in which a part of 15 consecutive bases at the 5' end region of SEQ ID NO: 61 and a part of 15 consecutive bases at the 3' end region thereof are complementarily paired, wherein the ninth base in SEQ ID NO: 61 is an unpaired base. It was found that gg583nt consisting of the sequence of SEQ ID NO: 61 and GG linked to the 5' end thereof served as a good substrate for methylation activity by Erm. The double-stranded RNA molecule consisting of the sequence of SEQ ID NO: 61 may contain a domain V structure of 23S rRNA.

Another aspect provides a double-stranded RNA molecule variant consisting of the sequence of SEQ ID NO: 61, in which all or part of 1 to 8 base pairs located between the end of the stem structure and/or the ninth base of SEQ ID NO: 61 are truncated.

According to an embodiment, the Erm may be at least one selected from the group consisting of ErmB, ErmE, and ErmS. The Erm may be expressed in bacteria of Firmicutes, *Bacteroides*, Proteobacteria, or Actinobacteria. For example, the ErmS and ErmE may be Erm proteins mainly expressed in Actinobacteria, and ErmB may be Erm proteins mainly expressed in bacteria of Firmicutes, but not limited thereto. More specifically, the bacteria expressing ErmB may include *Arcanobacterium pyogenes, Bacillus cereus, Bacteroides uniformis, Clostridium difficile, Clostridium perfringens, Enterococcus faecalis, Enterococcus faecium, Enterococcus hirae, Enterococcus* sp., *Escherichia coli, Gemella haemolysans, Gemella morbillorum, Lactobacillus crispatus, Lactobacillus fermentum, Lactobacillus johnsonii, Lactobacillus salivarius, Lactococcus garvieae, Macrococcus caseolyticus, Pediococcus acidilactici, Staphylococcus aureus, Staphylococcus intermedius, Staphylococcus lentus, Staphylococcus agalactiae, Streptococcus cristatus, Streptococcus gallolyticus, Streptococcus hyointestinalis, Streptococcus pneumoniae, Streptococcus pyogenes, Streptococcus sanguinis, Streptococcus* sp., *Streptococcus suis, Streptococcus thermophiles,* and *Streptococcus uberis*, (Phylogenetic analysis of rRNA methyltransferases, Erm and KsgA, as related to antibiotic resistance, H J Jin et al., FEMS Microbiol Lett 309 (2010) 151-162), but not limited thereto.

The double-stranded RNA molecule or a variant thereof can be used to identify a candidate substance's inhibition of methylation by Erm and the mode of action thereof, and thus can be used to develop inhibitors of antibiotic resistance expression. In addition, the double-stranded RNA molecule or a variant thereof may be used to guide further improvement or modification of previously developed inhibitor candidates. Alternatively, when the double-stranded RNA molecule or a variant thereof is administered together with an antibiotic, the expression of antibiotic resistance may be suppressed by inhibiting methylation via binding to Erm. In addition, the double-stranded RNA molecule or the variant thereof can also be used to determine a structure in which an Erm protein and an RNA are bound to form a complex. Based on the structures of the double-stranded RNA molecule alone or in the Erm protein-RNA complex obtained above, an inhibitor that mimics the RNA structure may be developed.

According to another aspect, provided is a composition for screening an antibiotic resistance inhibitor comprising at least one of the double-stranded RNA molecules and variants thereof.

According to an embodiment, the antibiotics may be a macrolide-lincosamide-streptogramin B ($MLS_B$) class antibiotic.

According to another aspect, there is provided a composition for determining a structure of an Erm protein bound to a substrate thereof or a complex of an Erm protein and a substrate thereof, comprising at least one of the double-stranded RNA molecules and variants thereof.

According to another aspect, there is provided a method for screening an antibiotic resistance expression inhibitor, comprising the steps of: contacting the double-stranded RNA molecule or a variant thereof with a candidate substance and an Erm protein; and identifying inhibition of methylation by the candidate substance.

In an embodiment of the present invention, the contacting step may include contacting a double-stranded RNA molecule or a variant thereof and a candidate substance; and an Erm protein with a candidate substance; contacting a double-stranded RNA molecule or a variant thereof with an Erm protein and a candidate substance.

In an embodiment of the present invention, the contactings in the contacting step may be conducted in different orders.

In an embodiment of the present invention, the double-stranded RNA molecule is a double-stranded RNA molecule in which a first strand consisting of the sequence of SEQ ID NO: 1 and a second strand consisting of the sequence of SEQ ID NO: 2 are paired while forming 13 base pairs,
the first and second bases of SEQ ID NO: 1 form a 5' overhang,
the 19th to 22nd bases of SEQ ID NO: 1 form a 3' overhang,
the 11th base of SEQ ID NO: 1 is an unpaired base, and the variant may comprise one or more of the following mutations in the double-stranded RNA molecule:
(a) deletion of all or part of the 5' overhang of the first strand;
(b) truncation of all or part of base pairs between the 5' end of the first strand and the 11th unpaired base of SEQ ID NO: 1;
(c) truncation of all or part of base pairs between the 5' end of the first strand and the 11th unpaired base of SEQ ID NO: 1 and deletion of the first and second bases of SEQ ID NO: 1;
(d) truncation of all or part of base pairs between the 5' end of the first strand and the 11th unpaired base of SEQ ID NO: 1 and addition of a tetraloop sequence to cap the remaining end of the base pairs after truncation;
(e) truncation of all or part of base pairs between the 5' end of the first strand and the 11th unpaired base of SEQ ID NO: 1, addition of a tetraloop sequence to the truncated end of the base pairs, and deletion of the first and second bases of SEQ ID NO: 1;
(f) truncation of part of base pairs between the 5' end of the first strand and the 11th unpaired base of SEQ ID NO: 1 and 11$^{th}$ unpaired base, addition of a tetraloop sequence to the side of the truncation;

(g) addition of a tetraloop sequence linked to all of base pairs between the 5' end of the first strand and the 11th unpaired base of SEQ ID NO: 1;

(h) addition of a tetraloop sequence linked to all of base pairs between the 5' end of the first strand and the 11th unpaired base of SEQ ID NO: 1 and truncation of the 11th unpaired base, and deletion of the first and second bases of SEQ ID NO: 1;

(i) deletion of all or part of 3' overhang of the first strand; and (j) addition of a hairpin loop formed by linking the 3' overhang of the first strand to the 5' end of the second strand.

According to a specific embodiment, the double-stranded RNA molecule or a variant thereof may be:

(a) a double-stranded RNA molecule consisting of 3 base pairs in which the sequence of SEQ ID NO: 6 and a sequence complementary thereto are paired, or part thereof, (b) a double-stranded RNA molecule consisting of 5 base pairs in which the sequence of SEQ ID NO: 7 and a sequence complementary thereto are paired, or part thereof, (c) a double-stranded RNA molecule consisting of 8 base pairs in which the sequence of SEQ ID NO: 8 and a sequence complementary thereto are paired, or part thereof, (d) a double-stranded RNA molecule in which the sequence of SEQ ID NO: 9 and the sequence of SEQ ID NO: 10 are paired or a variant thereof in which a portion of the double-stranded RNA molecule is deleted;

(e) a single-stranded RNA molecule consisting of a sequence of SEQ ID NO: 5 in which the 6th and 7th bases are removed, or a partial sequence thereof, (f) a double-stranded RNA molecule variant in which the sequence of SEQ ID NO: 11 and the sequence of SEQ ID NO: 12 are paired, or a variant thereof in which a portion of the double-stranded RNA molecule is deleted;

(g) a double-stranded RNA molecule in which the sequence of SEQ ID NO: 13 and the sequence of SEQ ID NO: 14 are paired, or a variant thereof in which a portion of the double-stranded RNA molecule is deleted;

(h) a double-stranded RNA molecule in which the sequence of SEQ ID NO: 1 and the sequence of SEQ ID NO: 2 are paired, or a variant thereof in which a portion of the double-stranded RNA molecule is deleted;

(i) a double-stranded RNA molecule in which the sequence of SEQ ID NO: 15 and the sequence of SEQ ID NO: 16 are paired, or a variant thereof in which a portion of the double-stranded RNA molecule is deleted; and (j) a double-stranded RNA molecule in which the sequence of SEQ ID NO: 17 and the sequence of SEQ ID NO: 18 are paired, or a variant thereof in which a portion of the double-stranded RNA molecule is deleted.

The screening may include screening a new antibiotic resistance inhibitor or an improvement or modification from existing antibiotic resistance expression inhibitors.

According to a specific embodiment, the inhibition of methylation may include inhibiting the interaction of the double-stranded RNA molecule or a variant thereof and/or the Erm protein.

According to an embodiment, inhibiting the interaction may be inhibition of the interaction between the Erm protein and at least one of the first to third Erm interaction sites. The first to third Erm interaction sites are as described above.

According to an embodiment, the Erm may be one or more selected from the group consisting of ErmB, ErmE, and ErmS.

According to an embodiment, the antibiotic resistance inhibitor may inhibit the antibiotic resistance of bacteria belonging to Firmicutes, *Bacteroides*, Proteobacteria and Actinobacteria. Specific examples of the bacteria belonging to Firmicutes are as described above.

According to another aspect, provided is a composition for inhibiting the expression of antibiotic resistance, comprising at least one of the following double-stranded or single-stranded RNA molecules: (a) a double-stranded RNA molecule consisting of 3 base pairs in which the sequence of SEQ ID NO: 6 and a sequence complementary thereto are paired, or part thereof, (b) a double-stranded RNA molecule consisting of 5 base pairs in which the sequence of SEQ ID NO: 7 and a sequence complementary thereto are paired, or part thereof, (c) a double-stranded RNA molecule consisting of 8 base pairs in which the sequence of SEQ ID NO: 8 and a sequence complementary thereto are paired, or part thereof, (d) a double-stranded RNA molecule in which the sequence of SEQ ID NO: 9 and the sequence of SEQ ID NO: 10 are paired or a variant thereof in which a portion the double-stranded RNA molecule is deleted;

(e) a single-stranded RNA molecule consisting of a sequence of SEQ ID NO: 5 in which the 6th and 7th bases are removed, or a partial sequence thereof, (f) a double-stranded RNA molecule variant in which the sequence of SEQ ID NO: 11 and the sequence of SEQ ID NO: 12 are paired, or a variant thereof in which a portion of the double-stranded RNA molecule is deleted;

(g) a double-stranded RNA molecule in which the sequence of SEQ ID NO: 13 and the sequence of SEQ ID NO: 14 are paired, or a variant thereof in which a portion of the double-stranded RNA molecule is deleted;

(h) a double-stranded RNA molecule in which the sequence of SEQ ID NO: 1 and the sequence of SEQ ID NO: 2 are paired, or a variant thereof in which a portion of the double-stranded RNA molecule is deleted;

(i) a double-stranded RNA molecule in which the sequence of SEQ ID NO: 15 and the sequence of SEQ ID NO: 16 are paired, or a variant thereof in which a portion of the double-stranded RNA molecule is deleted; and (j) a double-stranded RNA molecule in which the sequence of SEQ ID NO: 17 and the sequence of SEQ ID NO: 18 are paired, or a variant thereof in which a portion of the double-stranded RNA molecule is deleted.

Referring to FIG. 1, the present inventors found that truncation or modification of the first to third Erm interaction sites in a double-stranded RNA molecule led to significant reduction or elimination of the methylation activity of an Erm protein. Therefore, the expression of antibiotic resistance of bacteria may be inhibited via blocking the interaction of the Erm protein with a double-stranded RNA molecule consisting of a first Erm interaction site, a double-stranded RNA molecule consisting of a second Erm interaction site, a double-stranded RNA molecule consisting of a minimum substrate site, a double-stranded RNA molecule consisting of a first Erm interaction site and a second Erm interaction site; a single-stranded RNA molecule consisting of a hairpin loop sequence or a sequence with 2 CC nucleotides removed from the 3' end thereof, a double-stranded RNA molecule consisting of a first Erm interaction site, a second Erm interaction site, and a minimum substrate site; a double-stranded RNA molecule consisting of a second Erm interaction site and a minimum substrate site; a double-stranded RNA molecule consisting of a second Erm interaction site, a minimum substrate site, and a third Erm interaction site; a double-stranded RNA molecule consisting of a minimum substrate site and a third Erm interaction site; and a double-stranded RNA molecule consisting of a first Erm interaction site, a second Erm interaction site, a minimum substrate site, and a third Erm interaction site.

According to an embodiment, the double-stranded RNA molecule of (d) may be a minimum substrate, specifically a substrate in which the 2nd to 4th bases of SEQ ID NO: 9 and the 5th to 7th bases of SEQ ID NO: 9 are complementarily paired, and the 6th to 7th bases of SEQ ID NO: 10 and the 1st to 2nd bases of SEQ ID NO: 9 are complementarily paired. The structure of (d) may be understood with reference to FIG. 10.

The composition may include a pharmaceutically acceptable carrier. The pharmaceutically acceptable carrier may include, but is not limited to, physiological saline, polyethylene glycol, ethanol, vegetable oil, Ringer's solution, dextrose solution, glycerol and isopropyl myristate.

The composition may be prepared as a pharmaceutical preparation such as a therapeutic adjuvant, and may be prepared in a unit dose form by formulating with at least one selected from the group consisting of pharmaceutically acceptable carriers, diluents and excipients, or prepared by incorporating the same into a multi-dose container. The composition may be in the form of solutions, suspensions or emulsions in oil or aqueous medium, or may be in the form of extracts, powders, granules, tablets or capsules. The composition may further include a dispersing agent or a stabilizing agent.

The pharmaceutically acceptable carrier may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil but not limited thereto.

The pharmaceutical composition may further include additives known in the art in addition to the above ingredients. For example, at least one selected from the group consisting of lubricants, wetting agents, sweetening agents, flavoring agents, emulsifying agents, suspending agents, diluents, solubilizing agents, binders, disintegrating agents and preservatives, may be further included, but not limited thereto.

The composition is not limited in the mode of administration as long as a target tissue can be reached. For example, the composition may be administered orally or parenterally, and in the case of parenteral administration, the composition may be administered by skin application, rectal injection, intravenous injection, subcutaneous injection, intramuscular injection, intraperitoneal injection, transdermal administration, and the like. The composition can suppress the expression of resistance of bacteria by administering in combination with an antibiotics.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 4A shows a result for ErmS, FIG. 4B shows a result for ErmE, and FIG. 4C shows a result for ErmB;

FIGS. 8A-8C show the methylation activity of Erm proteins for 24 nt, 23 nt, 22 nt-II, 21 nt, 20 nt-II, and the like;

DETAILED DESCRIPTION

Figure 1:
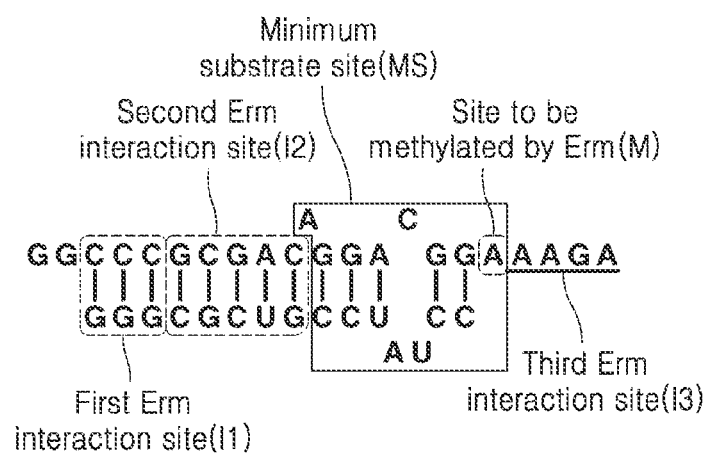
FIG. 1 shows the sequence and structure of a double-stranded RNA molecule according to an embodiment wherein I1 consists of 3 base pairs between 3rd to 5th bases of SEQ ID NO: 1 and the bases complementary thereto, I2 consists of 5 base pairs between 6th to 10th bases of SEQ ID NO: 1 and the bases complementary thereto, MS consists of AGGACGG in $11^{th}$ to $18^{th}$ positions of SEQ ID NO: 1 paired with CCUAUCC in the $1^{st}$ to $5^{th}$ positions of SEQ ID NO: 2 with C in $15^{th}$ position of SEQ ID NO: 1 and AU in $3^{rd}$ and $4^{th}$ positions of SEQ ID NO: 2 respectively forming an internal loop, M is adenine in the $19^{th}$ position of the SEQ ID NO: 1, which is marked as circled A, and I3 consists of the 19th to 22nd bases of SEQ ID NO: 1.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, one or more specific embodiments will be described in more detail through examples. However, these examples are for illustrative purposes of one or more embodiments, and the scope of the present invention is not limited to these examples.

Preparation of Experimental Materials

E. coli DH5a (Promega, Madison, WI, USA) and BL21 (DE3) (Novagen, Madison, WI, USA) were used for cloning and expression of His6-tagged Erm protein. Domain V of 23S rRNA was cloned from Bacillus subtilis BD170 and the sequence thereof was compared with the sequence published in the Gutell Lab's Comparative RNA Website and found 3 differences in the sequence, two mutations (C2203G and U2629A) and one nucleotide deletion (ΔC2473). A GenBank search with the query identified 19 identical sequences, but only two of them exactly corresponded to the one in the Gutell Lab's CRW site. Restriction endonucleases and DNA-modifying enzymes were purchased from New England BioLabs (Beverly, MA, USA) and used according to the manual. LB medium and Bacto Agar for bacterial culture were purchased from Difco Laboratories (Detroit, MI, USA).

Taq polymerase and nucleotides used for PCR were purchased from TaKaRa Shuzo Co. (Otsu, Shiga, Japan). Spermine, Triton X-100 and polyethylene glycol (PEG, molecular weight, 8,000) used for in vitro transcription were purchased from Sigma Chemical Co. (St. Louis, MO, USA) and nucleotides were purchased from TaKaRa Shuzo Co. T7 RNA polymerase in house was used. Chemically synthesized ribooligonucleotides were purchased from Bioneer Co. (Daejeon, Korea). His-Bind Resin used was Novagen's product. Acrylamide, bis-acrylamide, ammonium persulfate and TEMED (N,N,N',N'-tetramethylethylenediamine) used for polyacrylamide gel electrophoresis were purchased from Bio-Rad (Hercuyles, CA, USA). Common substances used, such as salts, buffer components, agarose and antibiotics, were Sigama products.

Experimental Method

1. Preparation of Erm Expression Vector (1) Preparation of ErmS Expression Vector and ErmE Expression Vector Expression vector (pHJJ105) and transformed E. coli HJJ105 for overexpression of ErmS, and expression vector pHJJ202 and transformed E. coli HJJ202 for overexpression of ErmE were prepared as previously disclosed (Recognition site generated by natural changes in Erm proteins leads to unexpectedly high susceptibility to chymotrypsin. Purification and biochemical characterization of the ErmSF macrolide-lincosamide-streptogramin B resistance factor protein expressed as a hexahistidine-tagged protein in Escherichia coli).

(1) Preparation of ErmB Expression Vector

To construct the ErmB expression vector, pVA838 plasmid DNA (see a cloning vector able to replicate in Escherichia coli and Streptococcus sanguis) was used as a DNA template, and the forward primer consisting of SEQ ID NO: 19 and the reverse primer consisting of SEQ ID NO: 20 were used to amplify the ErmB protein by PCR. The primer sequences were modified to include the restriction site of NdeI (5'-CATATG-3') and the restriction site of XhoI (5'-CTCGAG-3') overlapped with the Met start codon. The PCR amplification product was digested with NdeI and XhoI restriction enzymes, and the DNA fragment containing an ermB gene was ligated to the pET23b NdeI-XhoI site. The prepared ErmB plasmid was named pHJJ302. The sequence of the cloned gene was analyzed to confirm whether the gene was correctly inserted in-frame.

The double-stranded RNA molecule of the present invention serves as a substrate for the methylation activity by Erm, and thus can be used to test whether a candidate substance inhibits methylation by Erm, and can be used for development of antibiotic resistance inhibitors.

TABLE 2

| SEQ ID NO | DNA Oligonucleotide | Sequence (5' > 3') |
|---|---|---|
| SEQ ID NO: 19 | Forward primer for preparing ErmB expression vector | GGAATTCCATATGAACAAAAACATCAAA TACTCTCAAAACTTTTTAACGAAT |
| SEQ ID NO: 20 | Reverse primer for preparing ErmB expression vector | CCGCTCGAGTTTCCTCCCGTTAAATA ATAG |
| SEQ ID NO: 21 | Oligo 1: Forward primer for cloning rRNA | GGAATTCTAATACGACTCACTATAG |
| SEQ ID NO: 22 | Oligo 1-1: Reverse primer for cloning rRNA | GGAATTCTAATACGACTCACTATA |
| SEQ ID NO: 23 | Oligo 2: Forward primer for cloning gg583nt DNA | CGACTCACTATAGGCCCGCGACAGGACG GAAAGAC |
| SEQ ID NO: 24 | Oligo 2-1: Forward primer for cloning A2058G gg583nt DNA | CGACTCACTATAGGCCCGCGACAGGACG GGAAGAC |
| SEQ ID NO: 25 | Oligo 2-2: Forward primer for cloning A2058G gg583nt DNA | CGACTCACTATAGGCCCGCGACAGGACG GCAAGAC |
| SEQ ID NO: 26 | Oligo 2-3: Forward primer for cloning A2058U gg583nt DNA | CGACTCACTATAGGCCCGCGACAGGACG GTAAGAC |
| SEQ ID NO: 27 | Oligo 3: Reverse primer for cloning gg583-nt DNA | GGGACCATGGCCGGCCCCGCGACGGATA GGGACCG |
| SEQ ID NO: 28 | Oligo 4: Reverse primer for cloning rRNA DNA | CAGCGAGGAGGCTGGGACCATGGCCGGC |
| SEQ ID NO: 29 | Oligo 5: Reverse primer for cloning rRNA DNA | GCTCTAGAGTCCCATTCGCCATTACCGAG GGACGGTCCCCTCGGAATG |
| SEQ ID NO: 30 | Oligo 6: Forward primer for cloning 577nt DNA | CGACTCACTATAGCGACAGGACGGAAAG ACCCC |
| SEQ ID NO: 31 | Oligo 7: Reverse primer for cloning 577nt DNA | GGGACCATGGCCGGCGCGACGGATAGGG ACCGAAC |
| SEQ ID NO: 32 | Oligo 8: Forward primer for cloning 577nt DNA | CGACTCACTATAAGGACGGAAAGACCCC GTGG |
| SEQ ID NO: 33 | Oligo 8-1: Forward primer for cloning 567nt DNA | CGACTCACTATAAGGACGGGAAGACCCC GTGG |
| SEQ ID NO: 34 | Oligo 8-2: Forward primer for cloning 567nt DNA | CGACTCACTATAAGGACGGCAAGACCCC GTGG |
| SEQ ID NO: 35 | Oligo 8-3: Forward primer for cloning 567nt DNA | CGACTCACTATAAGGACGGTAAGACCCC GTGG |
| SEQ ID NO: 36 | Oligo 8-4 | CGACTCACTATACGGACGGAAAGACCCC GTGG |
| SEQ ID NO: 37 | Oligo 8-5 | CGACTCACTATATGGACGGAAAGACCCC GTGG |

TABLE 2-continued

| SEQ ID NO | DNA Oligonucleotide | Sequence (5' > 3') |
|---|---|---|
| SEQ ID NO: 38 | Oligo 9: Forward primer for cloning 566nt DNA | CGACTCACTATAGGACGGAAAGACCCCGTGGAG |
| SEQ ID NO: 39 | Oligo 10: Reverse primer for cloning 567/566nt DNA | GGGACCATGGCCGGCGGATAGGGACCGAAC |
| SEQ ID NO: 40 | Oligo 11: Forward primer for cloning gg37nt DNA | CGACTCACTATAGGCCCGCGACAGGACGGAAAGACCCCTATCCGTCGCG |
| SEQ ID NO: 41 | Oligo 12: Reverse primer for cloning gg37nt DNA | GGGACCATGGCCGGCCCCGCGACGGATAGGGGTCTTTCCG |
| SEQ ID NO: 42 | Oligo 13: Forward primer for cloning g21nt DNA | CGACTCACTATAGAGGACGGAAAGACCCCTATCCGCCGGCCATGGTCCC |
| SEQ ID NO: 43 | Oligo 13-1: Forward primer for cloning g21nt(A2058G) DNA | CGACTCACTATAGAGGACGGGAAGACCCCTATCCGCCGGCCATGGTCCC |
| SEQ ID NO: 44 | Oligo 13-2: Forward primer for cloning g21nt(A2058C) DNA | CGACTCACTATAGAGGACGGCAAGACCCCTATCCGCCGGCCATGGTCCC |
| SEQ ID NO: 45 | Oligo 13-3: Forward primer for cloning g21nt(A2058U) DNA | CGACTCACTATAGAGGACGGTAAGACCCCTATCCGCCGGCCATGGTCCC |
| SEQ ID NO: 46 | Oligo 13-4: Forward primer for cloning g21nt(A2051C) DNA | CGACTCACTATAGCGGACGGAAAGACCCCTATCCGCCGGCCATGGTCCC |
| SEQ ID NO: 47 | Oligo 13-5: Forward primer for cloning g21nt(A2051U) DNA | CGACTCACTATAGTGGACGGAAAGACCCCTATCCGCCGGCCATGGTCCC |
| SEQ ID NO: 48 | Oligo 14: Forward primer for cloning 20nt-I DNA | CGACTCACTATAGGACGGAAAGACCCCTATCCGCCGGCCATGGTCCC |
| SEQ ID NO: 49 | Oligo 15: Forward primer for cloning 24nt-I DNA | CGACTCACTATAGGCCTATCCTTCGGGACGGAAAGAGCCGGCCATGGTCCC |
| SEQ ID NO: 50 | Oligo 15-1: Forward primer for cloning 24nt (A2058G) DNA | CGACTCACTATAGGCCTATCCTTCGGGACGGGAAGAGCCGGCCATGGTCCC |
| SEQ ID NO: 51 | Oligo 15-2: Forward primer for cloning 24nt (A2058C) DNA | CGACTCACTATAGGCCTATCCTTCGGGACGGCAAGAGCCGGCCATGGTCCC |
| SEQ ID NO: 52 | Oligo 15-3: Forward primer for cloning 24nt (A2058U) DNA | CGACTCACTATAGGCCTATCCTTCGGGACGGTAAGAGCCGGCCATGGTCCC |
| SEQ ID NO: 53 | Oligo 16: Forward primer for cloning 22nt-I DNA | CGACTCACTATAGGCCTATCTTCGGACGGAAAGAGCCGGCCATGGTCCC |
| SEQ ID NO: 54 | Oligo 17: Forward primer for cloning 23nt-I DNA | CGACTCACTATAGGCCTATCCTTCGGGACGGAAAGGCCGGCCATGGTCCC |
| SEQ ID NO: 55 | Oligo 18: Forward primer for cloning 22nt-II DNA | CGACTCACTATAGGCCTATCCTTCGGGACGGAAAGCCGGCCATGGTCCC |
| SEQ ID NO: 56 | Oligo 19: Forward primer for cloning 22nt DNA | CGACTCACTATAGGCCTATCCTTCGGGACGGAAGCCGGCCATGGTCCC |

TABLE 2-continued

| SEQ ID NO | DNA Oligonucleotide | Sequence (5' > 3') |
|---|---|---|
| SEQ ID NO: 57 | Oligo 20: Forward primer for cloning 20nt-II DNA | CGACTCACTATAGGCCTATCCTTCGGGAC GGAGCCGGCCATGGTCCC |
| SEQ ID NO: 58 | Oligo 20-1: Forward primer for cloning 20nt-II(A2058G) DNA | CGACTCACTATAGGCCTATCCTTCGGGAC GGGGCCGGCCATGGTCC |
| SEQ ID NO: 59 | Oligo 20-2: Forward primer for cloning 20nt-II(A2058C) DNA | CGACTCACTATAGGCCTATCCTTCGGGAC GGCGCCGGCCATGGTCC |
| SEQ ID NO: 60 | Oligo 20-3: Forward primer for cloning 20nt-II(A2058U) DNA | CGACTCACTATAGGCCTATCCTTCGGGAC GGTGCCGGCCATGGTCC |

In Table 2, Oligo 15, 16, 17, 18, 19, and 20 include Ttcg for UUCG tetraloop.

2. Expression and Purification of Erm Protein

Each Erm protein was expressed in E. coli BL21 (DE3) having pHJJ105 (Erm S), pHJJ202 (Erm E) or pHJJ302 (Erm B) plasmid. Protein purification was performed as previously described with slight modifications (Purification and biochemical characterization of the ErmSF macrolide-lincosamide-streptogramin B resistance factor protein expressed as a hexahistidine-tagged protein in Escherichia coli). Briefly, cells were collected by centrifuging 100 ml of a culture and resuspending cell pelletsin buffer A (20 mM Tris-HCl [pH 7.0], 500 mM KCl and 5 mM imidazole). The collected cells were disrupted by sonication on ice. The sonication was performed by GEX-130 ultrasonic processor (130 W, 20 kHz) with a setting of 50% amplitude, 5 second pulse/10 second stop for a total of 5 minutes. The lysate was centrifuged to remove cell debris, such as inclusion bodies, and insoluble matter, and the supernatant was loaded onto a column containing His-Bind resin equilibrated with buffer A. Subsequently, the column was washed with buffer B (20 mM Tris-HCl [pH 7.0], 500 mM KCl and 100 mM imidazole) to remove unbound or misbound proteins, and the protein bound to the column was eluted with buffer C (20 mM Tris-HCl [pH 7.0], 500 mM KCl and 300 mM imidazole). In order to remove imidazole and salts from the eluted protein solution, the eluted protein solution was purified with a PD-10 desalting column according to the instructions of the manufacturer, GE Healthcare (Little Chalfont, Buckinghamshire, UK), and stored in 20 mM Tris-HCl (pH 7.0), 200 mM KCl, 1 mM EDTA and 50% glycerol at 20° C. The protein concentration was determined by bicinchoninic acid (BCA) protein assay.

3. Cloning for In Vitro Transcription of Various rRNAs

To produce transcripts with a homogeneous 3' end, a hepatitis delta virus (HDV) ribozyme was incorporated at the 3' end of the target RNA. To obtain a DNA fragment that encodes gg583nt, a first PCR amplification was performed with B. subtilis BD170 genomic DNA as a template, and oligo-2 and oligo-3 containing a part of the T7 promoter and 15 nt, a part of the 3' end sequence of HDV as forward and reverse primers. Oligo-2 and Oligo-3 comprise some sequences corresponding to 2043 to 2063 and 2606 to 2625 of B. subtilis 23S rRNA (E. coli coordinates: 2070 to 2090 and B. subtilis coordinates: 2634 to 2653).

A second PCR was performed by using, as Forward and Reverse primers, Oligo 1 and Oligo 4 containing the remaining portion of T7 promoter and EcoRI restriction site, and part of the sequence of HDV ribozyme. In order to make an XbaI restriction site positioned next to the HDV ribozyme, a third PCR was performed by using Oligo 1 and Oligo 5 having an HDV ribozyme sequence and an XbaI sequence as Forward and Reverse primers. After amplifying the DNA via the third PCR, the gg583nt DNA fragment was inserted into pUC19 by using restriction sites EcoRI and XbaI, cloned, and identified by sequencing. 577 nt (nucleotides 2046 to 2622 in E. coli coordinates), 567 nt (2051 to 2617; for each mutant of A2051 and A2058, an appropriate oligo-8 derivative was used) and 566 nt (2052 to 2617) were cloned in the same manner as the above-described method, except for primers. Oligo 1-1 was used in the second and third PCRs for 567nt.

Short DNA fragments for transcription of RNA substrates were obtained via an overlap extension method disclosed in [Wilson V T, Cundliffe E. 1999. Molecular analysis of tlrB, an antibiotic-resistance gene from tylosin-producing Streptomyces fradiae, and discovery of a novel resistance mechanism. J Antibiot (Tokyo) 52:288-296] with slight modification, and splicing. DNA fragments encoding gg37-nt RNA were also obtained with HDV ribozyme incorporated at the 3' end through a series of PCRs. A first PCR was performed by using Oligo 11 and Oligo 12, which are complementary sequences to each other to generate a template containing gg37-nt RNA, and then a second PCR and a third PCR were performed by using Oligo 1 and Oligo 4 as forward and reverse primers, in the same manner as above, thereby generating a gg37-nt DNA construct. By using Oligo 13 to Oligo 20 as forward primers and Oligo 4 as a reverse primer, PCRs were performed to generate g21nt, 20nt-I, 24nt, 22nt-I, 21nt and 20nt-II DNA constructs. In order to introduce genetic modification to A2051 and A2058, 24nt, 21nt and 20nt-II were subjected to a first PCR by using appropriate primers indicated in Table 2 above. To prepare a DNA fragment containing an EcoR1 restriction site and a T7 promoter sequence at the 5' end, and a complete ribozyme sequence and an XbaI restriction site at the 3' end, final PCR was performed by using the 8 different constructs obtained above as templates, Oligo 1 as a forward primer and Oligo 5 as a reverse primer. The resulting constructs were inserted into multiple cloning sites of EcoRI and XbaI of pUC19. In order to identify the inserted constructs, DNA sequencing was conducted, and primers for cloning rRNA-encoding DNA fragments are summarized in Table 2 above.

4. In Vitro Transcription of Substrate RNAs

RNA was transcribed by using the prepared plasmid as a template and a phage T7 RNA polymerase. For efflux transcription, the plasmid was linearized by using the XbaI restriction site. RNA transcripts were synthesized by using the linearized plasmid as a template. Specifically, transcription of the linearized plasmid as a template was performed in 500 µl mixed solution including 40 mM Tris-HCl (pH 8.1), 5 mM DTT (dithiothreitol), 1 mM spermine, 0.01% Triton X-100, 80 mg/ml PEG, 25 µg DNA template, 4 mM rNTPs (ribonucleoside triphosphates), 28 mM $MgCl_2$ and 10 µg T7 RNA polymerase (prepared in-house) at 37° C. for 4 hours. After the transcription, the transcripts were extracted by using phenolchloroform. The extracted transcripts were precipitated with ethanol and then resuspended in DEPD (diethyl pyrocarbonate) treated water. Thereafter, the concentration of $MgCl_2$ was adjusted to 40 mM, and the transcripts were subjected to three cycles of 1 min at 72° C., 5 min at 65° C., and 10 min at 37° C. to allow the transcripts to undergo self-truncation reactions of 3' end HDV ribozyme. After electrophoresis on 5% to 13% 7M urea-polyacrylamide gel, the size and integrity of the produced transcripts were confirmed by using UV. After the electrophoresis, a band of the correct size was extracted with TBE (Tris-borate-EDTA) and precipitated with ethanol. Thereafter, the precipitated RNA was dissolved in a self-folding buffer containing 50 mM HEPES-KOH [pH 7.5], 20 mM magnesium acetate, and 400 mM $NH_4Cl$ by heating at 65° C. for 10 minutes. Then, the dissolved RNA was cooled at 37° C. for 90 minutes or more to allow the RNA transcripts to be self-folded.

5. In Vitro Methylation Assay and Substrate Activity Measurement

By modifying the methods disclosed in papers: Kovalic D, Giannattasio R B, Jin H J, Weisblum B. 1994. 23S rRNA domain V, a fragment that can be specifically methylated in vitro by the ErmSF (TlrA) methyltransferase. J Bacteriol 176:6992-6998, Zhong P, Pratt S D, Edalji R P, Walter K A, Holzman T F, Shivakumar A G, Katz L. 1995. Substrate requirements for ErmC=methyltransferase activity. J Bacteriol 177:4327-4332, Jin H J, Yang Y D. 2002; Purification and biochemical characterization of the ErmSF macrolide-lincosamide-streptogramin B resistance factor protein expressed as a hexahistidine-tagged protein in *Escherichia coli*. Protein Expr Purif 25:149-159, Zalacain M, Cundliffe E. 1989; and [Methylation of 23S rRNA caused by tlrA (ermSF), a tylosin resistance determinant from *Streptomyces fradiae*. J Bacteriol 171:4254-4260, in vitro methylation of an RNA substrate by an Erm protein was performed.

For analysis over time, a reaction was carried out in 300 µl of a mixture containing 50 mM Tris-HCl (pH 7.5), 4 mM $MgCl_2$, 40 mM KCl, 10 mM dithiothreitol (DTT), 19.8 pmol S-adenosyl-L-methionine (SAM; specific activity, 80 Ci/mmol; PerkinElmer), 60 pmol rRNA transcript, and 60 pmol purified Erm protein. The volumes and components were sufficient to carry out 6 reactions. Specifically, components other than proteins in the mixture were mixed and incubated by preheating at 37° C. for at least 5 minutes, and then purified Erm proteins were added to a tube to minimize any delay in the start of the reaction. Every 5 minutes or more time points, to stop the reaction, the tube was cooled on ice containing 0.5 ml of 12% trichloroacetic acid, and 50 µl of the reaction was removed and a fresh 50 µl was added. To obtain methylated RNA, centrifugation was performed, and the resultant product was washed twice with 1.25 ml of ice-cold 6% trichloroacetic acid. After drying, the precipitate was extracted with 3 ml of scintillation fluid (Ultima Gold; Packard) and transferred to a counting vial. The remaining precipitate was extracted again with 75 µl of double-distilled water (DDW) heated to 50° C. to 60° C., and extracted again with 25 µl of preheated DDW. All of the extracts obtained were combined and counted with Tri-Carb 2900TR (Packard, Shelton, CT, USA).

Methylation analysis at a single time point was performed in the same manner as described above, except that the reaction volume was 50 µl and the incubation time was 1 hour. The experiment was repeated at least 3 times.

Methylation of a chemically synthesized ribonucletide was performed in the following manner. 60 pmol of upper strand (5'-AGGACGGA-3') and lower strand (5'-CC-UAUCC-3') were dissolved in 2 µl of a self-folding buffer, and annealed by sequential incubation at 50° C. for 5 min and 10° C. for 90 min. The annealed duplex RNA was analyzed for methylation in the same manner as described above, except for the incubation temperature (18° C.) and incubation time (1.5, 3, 6, 9, 12 and 15 hours).

The amounts of all reaction components were doubled in order to confirm the positive substrate activity obtained with a typical methylation experiment. Specifically, the amounts of reaction components were doubled, for example, 120 pmol annealed ribonucleotide, ErmS enzyme and 39.6 pmol SAM, and the methyl group-accepting activity was measured. In both experiments, substrate activity was identified by observing a concomitant increase in radioactivity from the substrate as the incubation time increased. In order to confirm the specific methylation of A2058, the methyl group-accepting activities of A2058C and A2058U were confirmed.

Example 1: Identification of Change in Methylation Activity by Distal Truncation from Target Adenine of Substrate The minimum substrate that can be methylated by three Erm proteins, ErmS, ErmB, and ErmE commonly include all or part of helix 73, and an inner loop and a loop sequence that links helix 73 and 74.

The present inventors gradually truncated helix 73 from the 5' end of the sense sequence (hereinafter referred to as distal region), and confirmed whether the methyl group of S-adenosyl-L-methionine (SAM) was transferred to the truncated substrate by using the Erm protein, and thus defined a terminal nucleotide of the distal region of helix 73, which can have activity on the Erm protein, in other words, be methylated by the Erm protein. Since there is a possibility that a site other than helix 73 in domain V compensates for the loss of contact of the truncated helix 73, the experiment was performed by including other sites in domain V.

Figure 2:
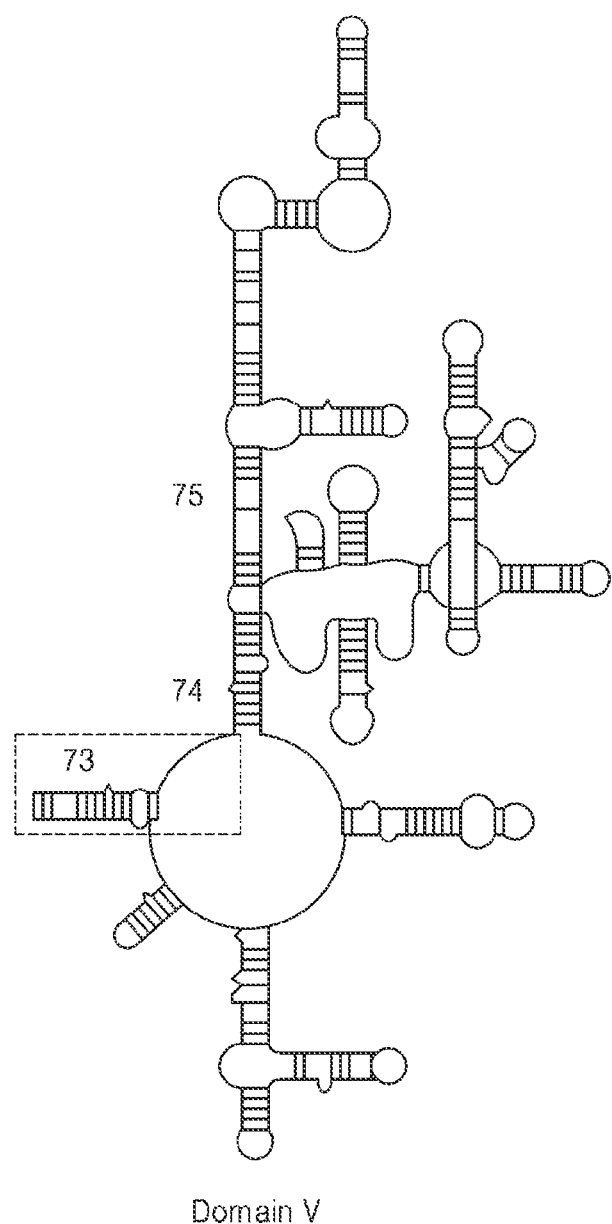
FIG. 2 shows domain V and the locations of helix 73 in domain V.
Figure 3:
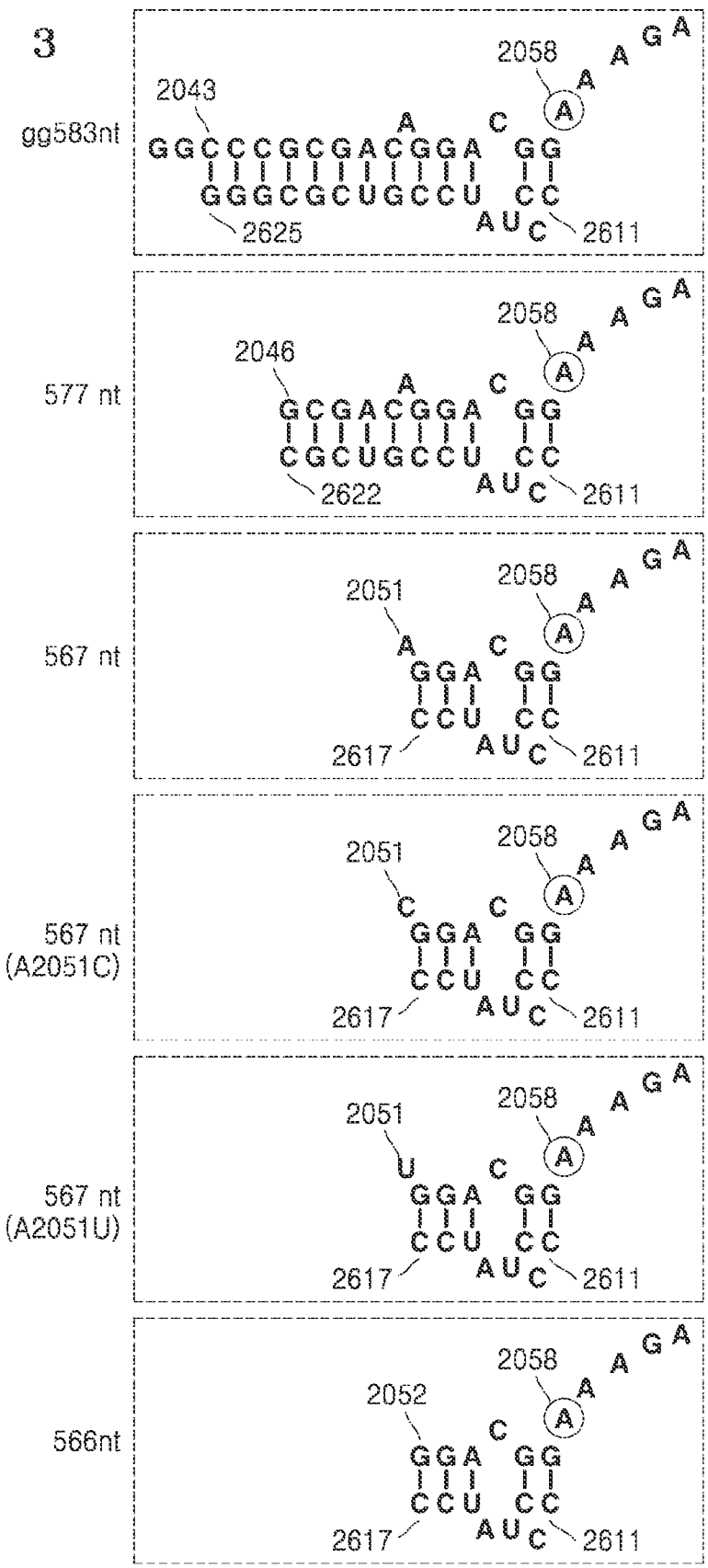
FIG. 3 shows the sequence and structure of RNA fragments prepared by gradually truncating from the end of helix 73 in domain V (the 5' end of the sense sequence), in which gg583nt, 577nt, 567nt, 567nt(A2051C), 567nt(A2051U) and 566nt contain the remaining structure of domain V after truncation as in FIG. 2, that is, a structure in which 3 base pairs (577nt) and 5 base pairs (567nt) are respectively removed from gg583nt, specifically, gg583nt consists of the sequence of SEQ ID NO: 61 and GG linked to the 5' end thereof, 577 nt refers to the RNA fragment obtained by removing a overhang GG and CCC base paired with GGG from the 5' end of gg583, 567 nt refers to the RNA fragment obtained by removing GCGAC base-paired with GUCGC from the 5' end of 577 nt, 567 nt(A2051C) and 567 nt(A2051U) refer to the variants of 567 nt wherein A marked as 2051 in 567 nt is replaced by C and U, respectively, and 566 nt refers to the RNA fragment obtained by removing A2051 from 567 nt.

FIGS. 2 and 3 show RNA fragments progressively truncated from the helix 73 region of domain V and the distal region of helix 73. RNA fragments were named gg583nt, 577nt, 567nt, and 566nt, respectively.

Table 3 below shows the results of confirming the activities of ErmS, ErmB, and ErmE for each RNA fragment under standard analysis conditions.

TABLE 3

| RNA | ErmS | ErmB | ErmE | Control, without protein |
|---|---|---|---|---|
| gg583 nt | +, 100, 562 ± 4,909 | +, 7,818 ± 459 | +, 95, 177 ± 907 | -, 105 ± 33 |
| gg583nt(A2058G) | -, 83 ± 13 | -, 67 ± 14 | -, 95 ± 20 | -, 79 ± 12 |
| gg583nt(A2058C) | -, 76 ± 29 | -, 82 ± 27 | -, 75 ± 26 | -, 82 ± 37 |
| gg583nt(A2058U) | -, 97 ± 12 | -, 91 ± 6 | -, 91 ± 12 | -, 95 ± 22 |
| 577 nt | +, 82, 899 ± 2,170 | +, 1, 283 ± 17 | +, 28, 464 ± 610 | -, 108 ± 12 |
| 567 nt | +, 680 ± 39 | -, 87 ± 31 | +, 267 ± 15 | -, 102 ± 12 |
| 567 nt(A2058G) | -, 96 ± 8 | ND | -, 87 ± 21 | -, 96 ± 8 |
| 567 nt(A2058C) | -, 87 ± 15 | ND | -, 101 ± 4 | -, 87 ± 29 |
| 567 nt(A2058U) | -, 79 ± 16 | ND | -, 96 ± 15 | -, 92 ± 28 |
| 567 nt(A2051C) | -, 79 ± 2 | ND | ND | -, 83 ± 14 |
| 567 nt(A2051U) | -, 86 ± 20 | ND | ND | -, 90 ± 16 |
| 566 nt | -, 103 ± 16 | ND | -, 84 ± 6 | -, 96 ± 8 |

According to Table 3, ErmS exhibited about 13 times higher methylation activity than ErmB by delivering 36.01% of SAM (3.3 pmol) to gg583nt.

577nt is an RNA fragment in which 3 base pairs (complementarily paired CCC and GGG) were further truncated from the distal region of gg583nt. The levels of reduction in the Erm activity for 577nt were different among the three types of Erm proteins. According to Table 3, ErmB showed above 84% reduction in the substrate activity by about 84%, ErmE about 70%, while ErmS showed only about 18% reduction.

567nt is an RNA fragment in which 5 more base pairs are removed from the distal region of 577nt. According to Table 3 and FIGS. 4A to 4C, ErmB lost methylation activity, ErmS exhibited 0.7% methylation activity, and ErmE exhibited 0.3% methylation activity. ErmS transferred 0.01 pmol from 3.3 pmol SMA and ErmE transferred 0.002 pmol from 3.3 pmol SMA.

566nt is an RNA fragment obtained by removing A2051 from 567nt. According to Table 3 and FIGS. 4A to 4C, removal of A2051 led to loss of the activity of the Erm protein therefor.

Figure 4A:
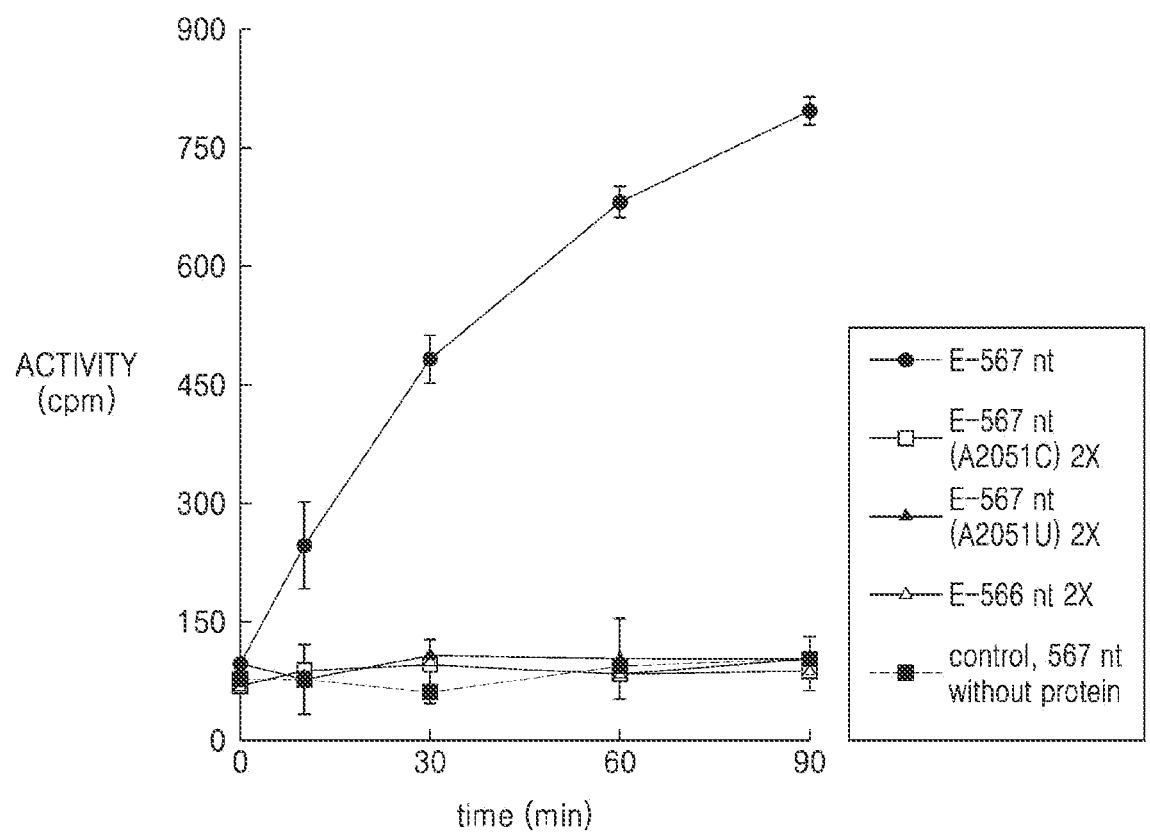
FIGS. 4A-4C shows the activity of three types of Erm proteins for 567nt and 566nt.
Figure 4B:
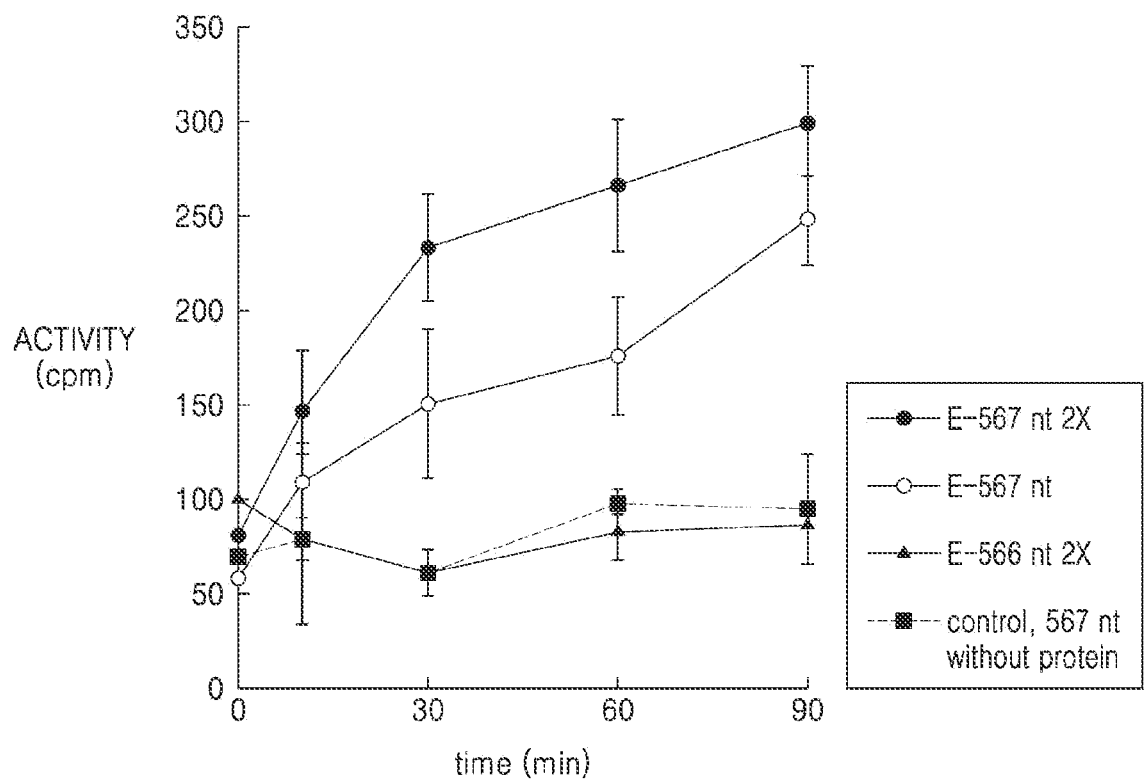
Figure 4C:
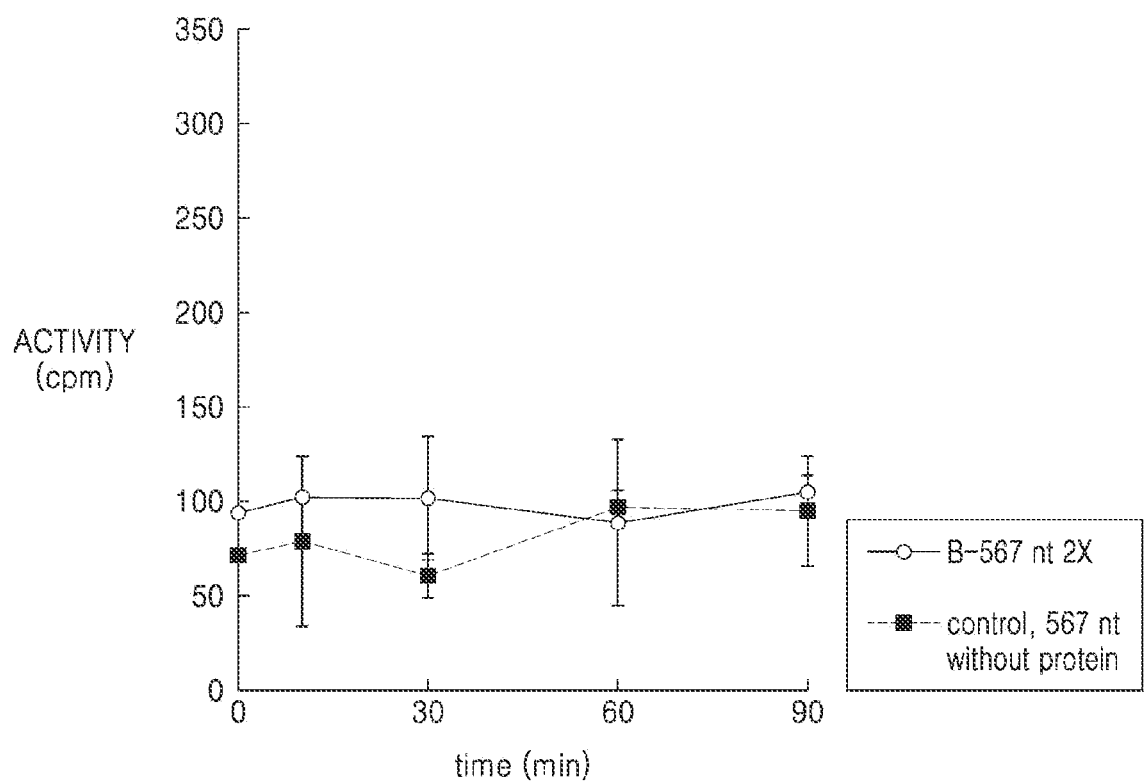

As shown in FIGS. 4A to 4C, the amount of ErmS used was doubled for 566nt, but no substrate activity was observed (S-566nt 2× in FIG. 4A). However, 567nt exhibited increase in activity as a substrate with increase in the contact time with ErmS (S-567nt in FIG. 4A), and doubling the amount of ErmE for 567nt increased the degree of methylation (E-567nt 2× of FIG. 4B), and thus it was determined that the residue farthest from the target adenine, which may affect the methylation activity by Erm, was A2051. (This finding was reconfirmed in Example 2 below.)

567nt (A2051C) and 567nt (A2051U) were prepared by substituting C or U for A2051 in 567nt. 567nt (A2051C) and 567nt (A2051U) also lost activity as a substrate for methylation by Erm. Therefore, it is considered that the reason for loss of the Erm methylation activity for 566nt from which A2051 is removed is not due to the structural change caused by the removal of A2051.

In addition, since the methylation activities of gg583 nt (A2058G), gg583 nt (A2058C), and gg583 nt (A2058U) were significantly reduced, it can be seen that methylation by the Erm protein specifically occurs in A2058.

According to the experimental results, the distal region of helix 73, specifically three terminal base pairs (base pairs between CCC and GGG, see gg583 nt and 577 nt), is expected to affect the target adenine methylation by the Erm protein via an allosteric effect and/or cooperativity with other structures of domain V. This is because the loss of activity is too significant to be considered caused by three terminal base pairs. Additionally, the loss of activity observed by the following removal of 5 base pairs is thought to be attributable to the observed allosteric effect and/or cooperativity along with the loss of essential interaction with the protein, as seen from the increased activity with addition of a tetraloop as an substitute for the 5 base pairs removed in Example 2 below, which is thought to be caused by increased binding with protein by the tetraloop.

Figure 5:
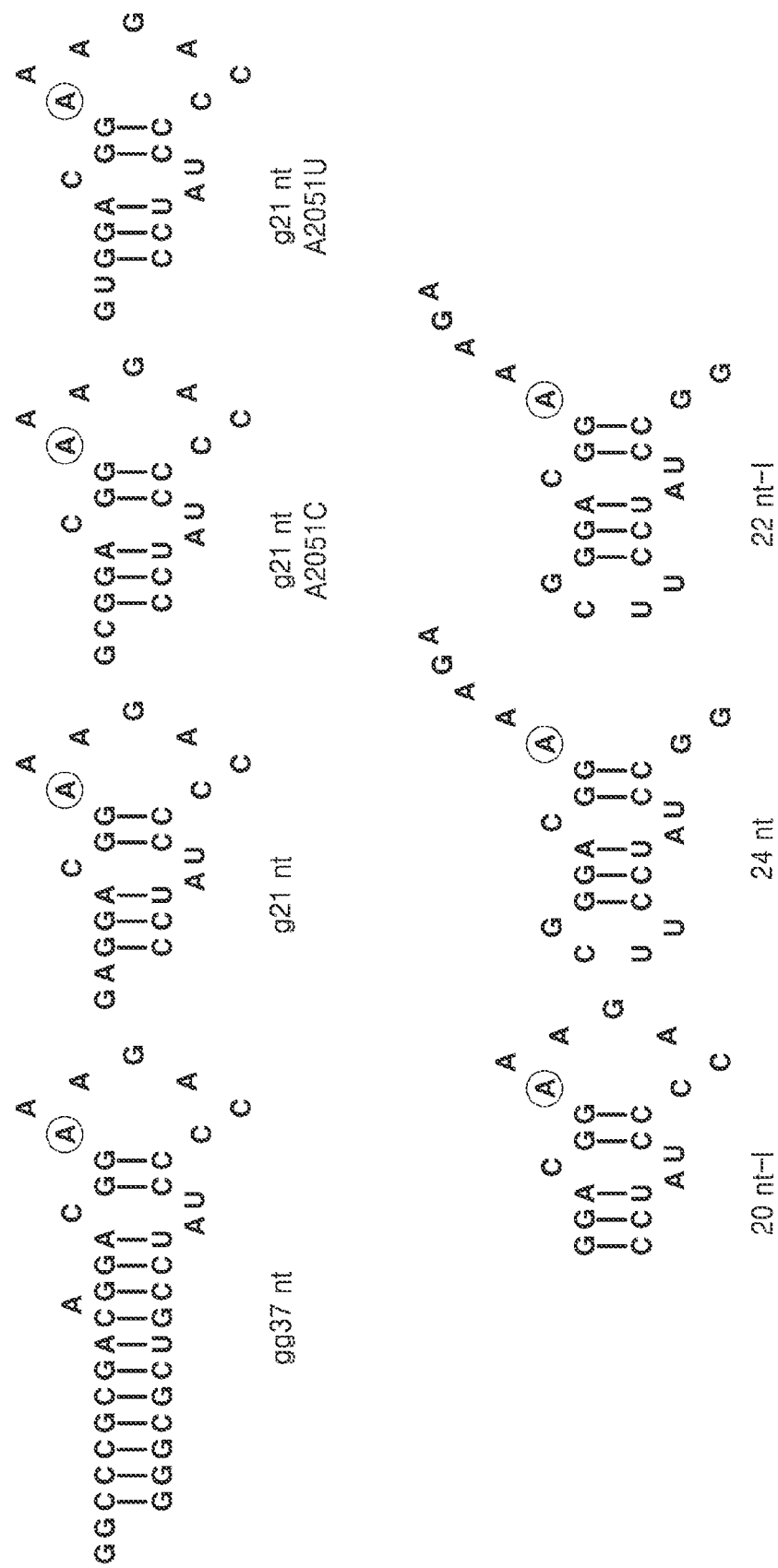
FIG. 5 shows a double-stranded RNA molecules in which the side of the 3' end of a sense sequence is capped with a 7 nt hairpin loop, and a double-stranded RNA molecules in which the side of the 5' end of a sense sequence is UUCG tetraloop-capped: gg37nt includes a 5'-GG overhang the first Erm interaction site (I1) consisting of 3 base pairs between the 3rd to 5th bases of SEQ ID NO: 1 and the bases complementary thereto, the second Erm interaction site (I2) consisting of 5 base pairs between 6th to 10th bases of SEQ ID NO: 1 and the bases complementary thereto, the minimum substrate site (MS) consisting of AGGACGGA in $11^{th}$ to $18^{th}$ positions of SEQ ID NO: 1 paired with CCUAUCC in the $1^{st}$ to $5^{th}$ positions of SEQ ID NO: 2 with C in $15^{th}$ position of SEQ ID NO: 1 and AU in $3^{rd}$ and $4^{th}$ positions of SEQ ID NO: 2 respectively forming an internal loop, and the third Erm interaction site (I3) in which loop sequence (7nt) tethering on the methylatable adenine side contains the natural loop sequence AAAGA (bold letter denotes the methylatable adenine and AAGA corresponds to 19th to 22nd bases of SEQ ID NO: 1) and extra CC nucleotides; g21nt has a 5'-unpaired G, the first Erm interaction site (I1) and the second Erm interaction site (I2) being removed from gg37nt; g21nt (A2051C) and g21nt (A2051U) have A2051 (the second nucleotide, A of the g21nt sense sequence) substituted with another nucleotide C or U; in 20nt-I, the first Erm interaction site (I1), the second Erm interaction site (I2), and A2051 were removed from gg37nt; In 24 nt, the hairpin loop in 20 nt-I was unleashed and instead, it was tethered with a tetraloop (UUCG) on the other side; and 22 nt-I, was formed through part of the base pairs, one base pair (GC) next to tetraloop, being removed from 24 nt.
Figure 6A:
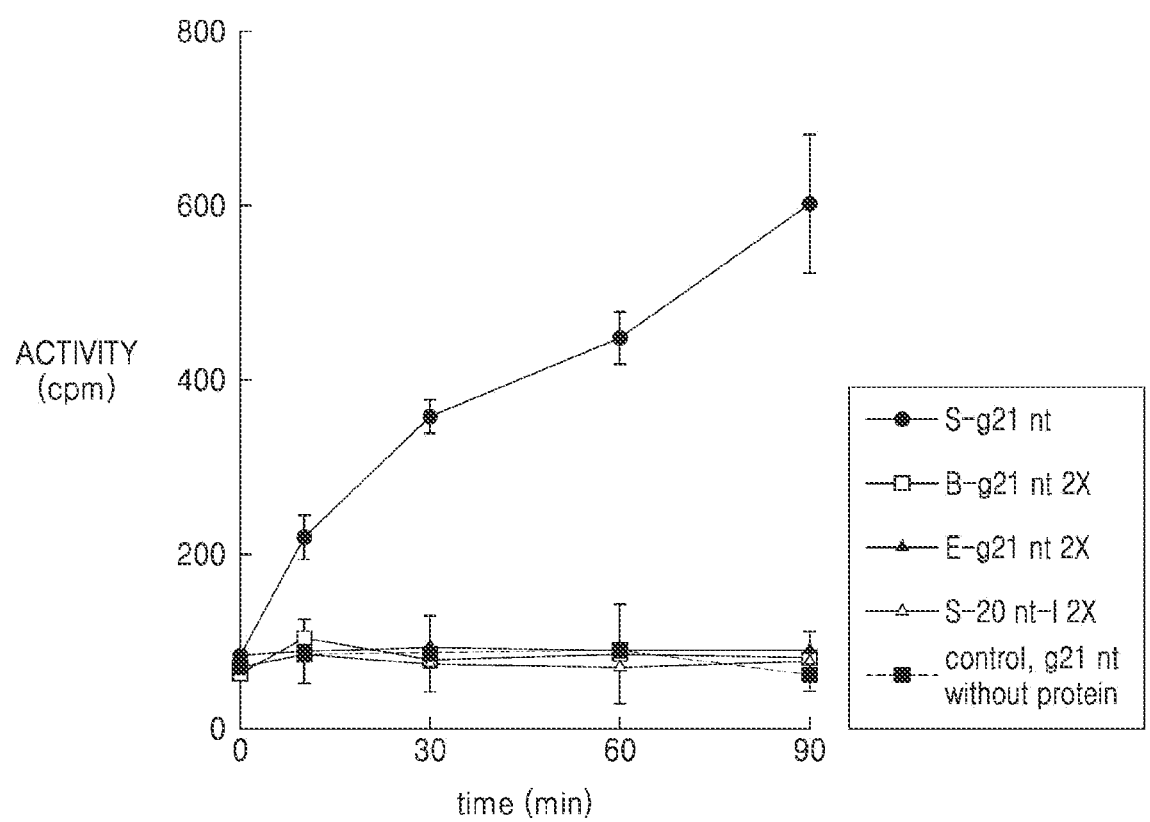
FIGS. 6A-6B show the activity of Erm proteins for g21 nt and its mutants.
Figure 6B:
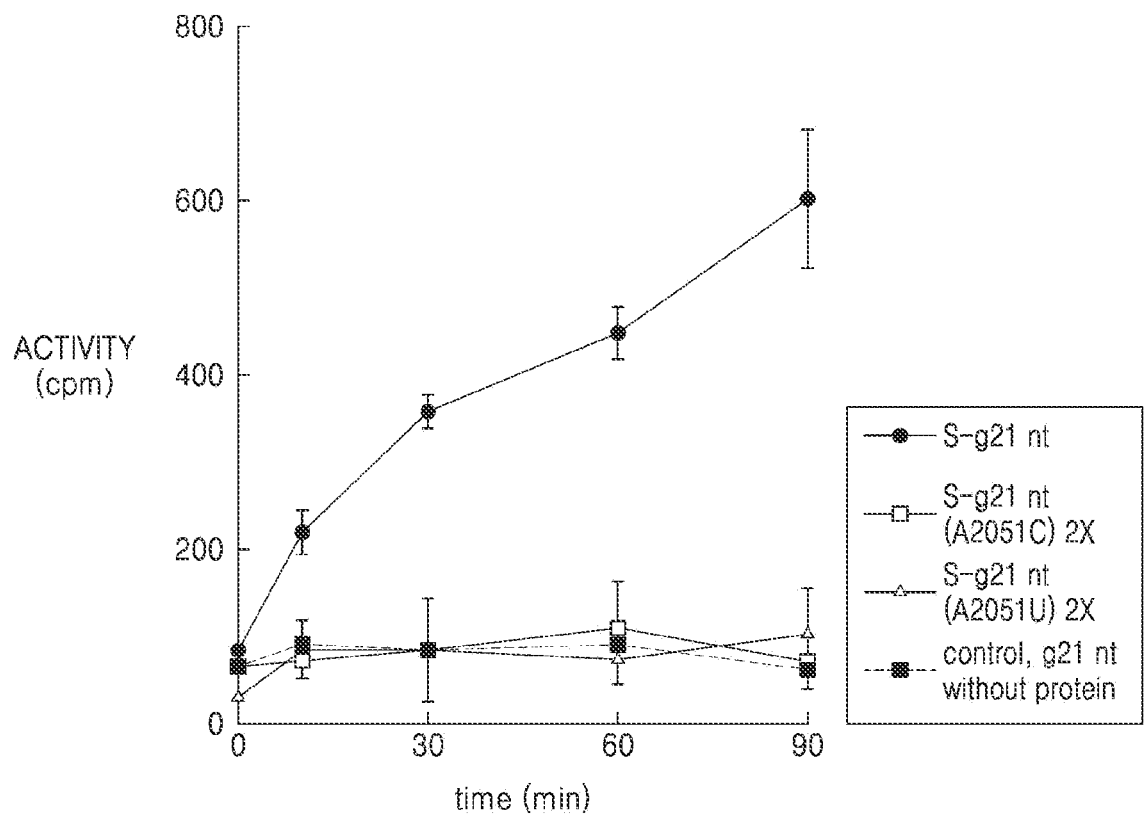

Example 2: Identification of Change in Methylation Activity by Hairpin Loop Capping of Substrate FIG. 5 shows an RNA fragment in which the 3'-end of the sense sequence of the double-stranded RNA of helix 73 is capped with a hairpin loop. gg37 nt, g21 nt, g21 nt A2051C, g21 nt A2051U, and 20 nt-1 are double-stranded RNA fragments in which the adenine A2058 for methylation is capped with a 7-nt hairpin loop. The sequence of the 7-nt hairpin loop is AAAGAcc and includes A2058. AAAGA is a natural sequence that links helix 73 and helix 74 of domain V. Each A that is circled is a adenine (A2058) to be methylated, and a lowercase cc is an artificially added sequence.

Table 4 below shows the results of confirming the activities of Erm proteins for the double-stranded RNA molecules in FIG. 5

TABLE 4

| RNA | ErmS | ErmB | ErmE | Control, without protein |
|---|---|---|---|---|
| gg37nt | +, 41, 083 ± 1.807 | +, 259 ± 40 | +, 3, 119 ± 395 | -, 74 ± 18 |
| g21nt | +, 449 ± 32 | -, 85 ± 19 | -, 91 ± 50 | -, 91 ± 9 |
| g21nt A2051C | -, 110 ± 53 | ND | ND | ND |
| g21nt A2051U | -, 73 ± 29 | ND | ND | ND |
| 20nt-1 | -, 69 ± 42 | ND | ND | ND |
| 24nt | +, 1,867 ± 144 | +, 337 ± 48 | +, 783 ± 116 | -, 105 ± 14 |
| 22nt-1 | -, 99 ± 25 | -, 67 ± 31 | -, 102 ± 8 | ND |

According to Table 4, all Erm proteins showed methylation activity for gg37 nt including the entire sequence of Helix 73. The g21 nt truncated with 3 base pairs (complementary pair of CCC and GGG) from the distal region were methylated by ErmS, but the methylation activity by ErmB was lost, which was consistent with the results for 567 nt. ErmE exhibited the methylation activity for 567 nt, but lost the activity for g21 nt. However, these observations are considered attributable to the limited conformation of the target adenine present in g21 nt.

Similar to the results observed in Example 1, all Erm proteins did not show any methylation activity for 20 nt-I with A2051 removed. Since substitution of A2051 in g21 nt with C or U lead to loss of any substrate activity, it is considered that the loss of substrate activity by the removal of A2051 is not due to a structural change.

However, when A2051 was removed and the distal side was capped with a UUCG tetraloop to form a hairpin, the methylation activity by all Erm proteins was significantly enhanced. According to Table 4, the activity of ErmS for 24 nt was about 4 times higher than that for g21 nt. Although not shown in the table, when the UUCG tetra-loop was replaced with the GCAA tetra-loop, the substrate activity was increased three times more than that of 24 nt with the UUCG tetra-loop. The activity of ErmE for 24 nt was three times higher than that for 567 nt. The activity of ErmB for 24 nt was much higher than that for gg37 nt. ErmB did not exhibit any methylation activity for g21 nt and 567 nt, but exhibited strong methylation activity for 24 nt capped with UUCG tetraloop, which was 1.3 times higher than the activity for gg37nt having most of the helix 73 sequence. This suggests that the affinities of the Erm protein with A2051 and surrounding bases thereof are important in methylating 23S rRNA.

Despite the increase in the substrate activity by UUCG tetraloop capping, removal of one of the base pairs located between UUCG tetraloop and A2058 resulted in loss of methylation activity (see 22 nt-I in Table 3). This means that the number of base pairs between A2051 and A2058 and distances thereof or base pairs per se have a significant effect on the substrate activity.

According to the experimental results, the cause for the decrease in activity by truncation up to A2051 is considered not only the loss of allosteric effect and cooperativity observed in Example 1 but also the loss of supplementary binding affinity between the enzyme and a region immediately outside the minimum substrate.

Example 3: Identification of Change in Methylation Activity by Loop Region Truncation of Substrate In Example 2, the capping of the 7nt hairpin loop sequence of the RNA fragment did not lead to loss of the methylation activity by Erm. Following the experiment, changes in the methylation activity were examined with gradual truncation of the 7 nt loop sequence from the 3'-end adenine.

Figure 7:
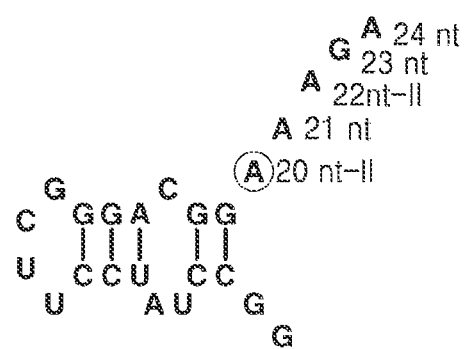
FIG. 7 shows 24 nt, and 23 nt, 22 nt-II, 21 nt, and 20 nt-II prepared by gradually removing the bases of the third Erm interaction site from the 3' end of the 24 nt, the 24 nt consists of a MS consisting of AGGACGG in $11^{th}$ to $17^{th}$ positions of SEQ ID NO: 1 paired with CCUAUCC in the $1^{st}$ to $5^{th}$ positions of SEQ ID NO: 2 with C in $15^{th}$ position of SEQ ID NO: 1 and AU in $3^{rd}$ and $4^{th}$ positions of SEQ ID NO: 2 respectively forming an internal loop, wherein a 5'-unpaired A removed, a UUCG tetraloop is capped at the 5' end, and an extra GG is added at the 5' end, and the third Erm interaction site consisting of 19th to 22nd bases of SEQ ID NO: 1.

In an RNA fragment capped with a UUCG tetraloop on the distal side, the hairpin loop sequence on the 3' side of the sense sequence was unleashed to prepare RNA fragments in which nucleotides were truncated one by one from the AAAGA sequence, and a change in methylation activity was examined (see FIG. 7).

Figure 8A:
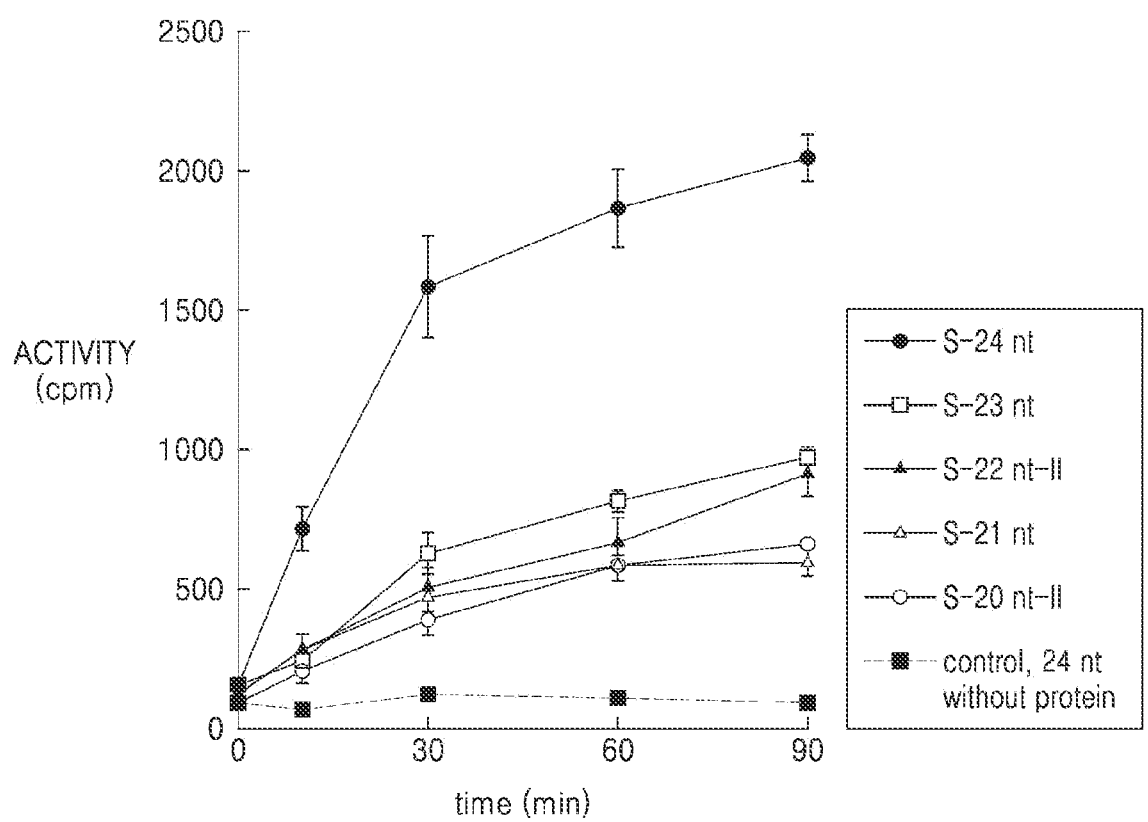
Figure 8B:
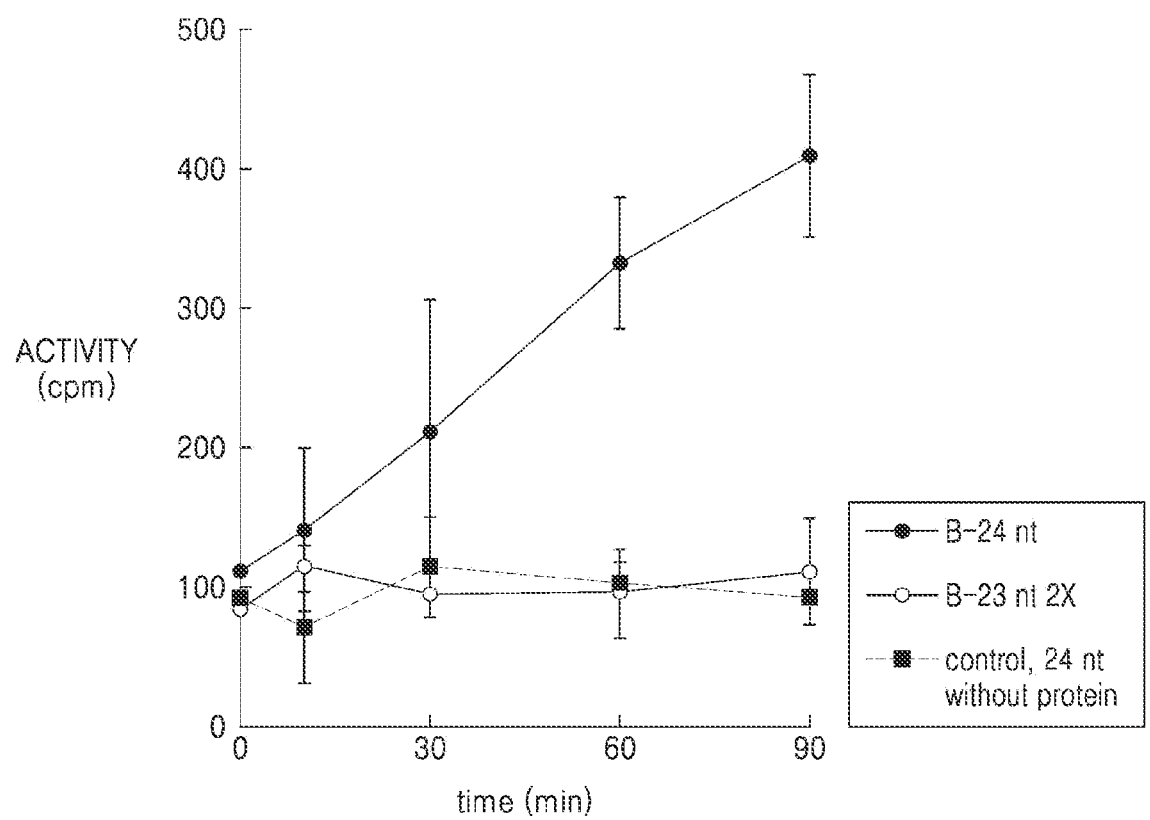
Figure 8C:
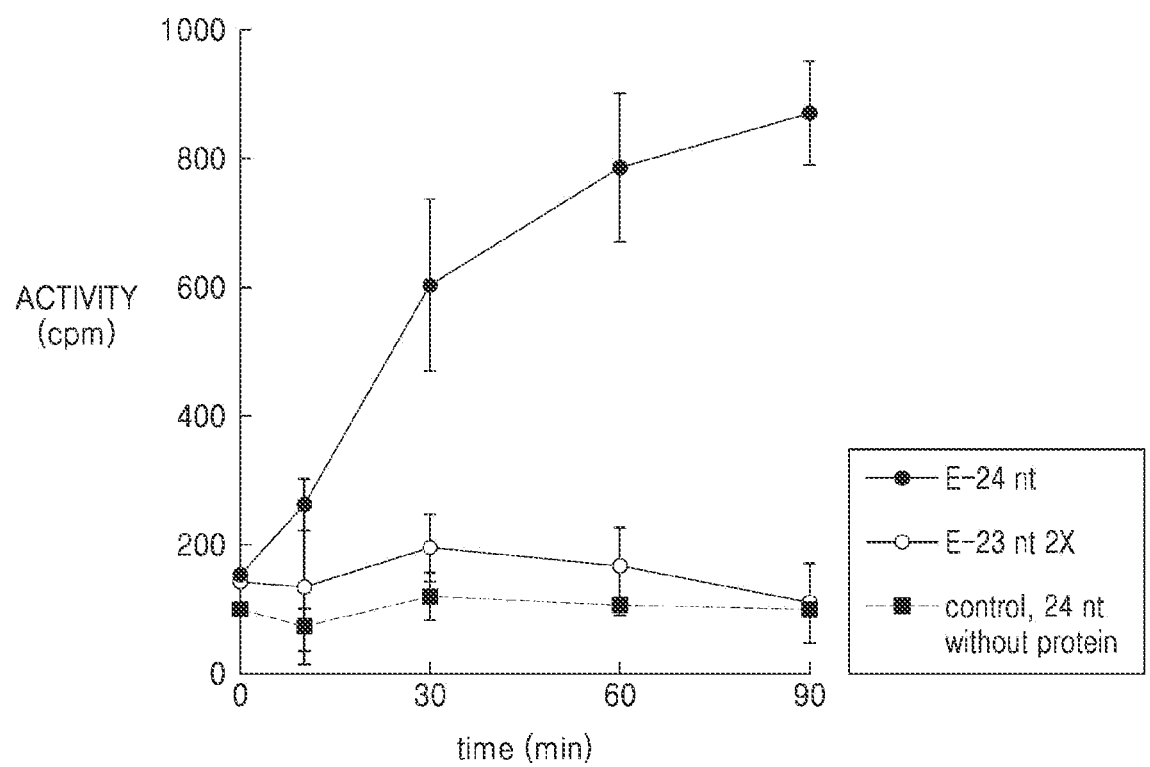

According to Table 5, the 24nt RNA fragment including the full sequence of AAAGA exhibited methylation activity by all Erm proteins. However, the 23nt RNA fragment containing AAAG (the 3'-end adenine residue removed from AAAGA) lost the methylation activity by ErmB and EmrE (see FIGS. 8A to 8C). ErmS still exhibited methylation activity after truncation proceeded to keep only the adenine for methylation. According to these results, the sequence that links helix 73 and helix 74 is thought to provide affinity for ErmB and ErmE to recognize and bind the target adenine, but it is considered that the affinity is not required for ErmS.

Based on the above results, it is considered that the loss of activity of ErmB and ErmE is not due to the structural change of RNA caused by truncation because ErmS showed methylation activity.

Figure 10:
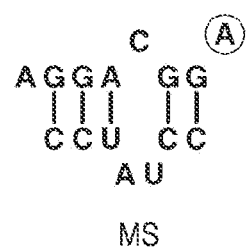
FIG. 10 shows a minimum substrate required for methylation by an Erm protein, wherein AGGACGG in $11^{th}$ to $17^{th}$ positions of SEQ ID NO: 1 pair with CCUAUCC in the $1^{st}$, $2^{nd}$, and $5^{th}$ to $7^{th}$ positions of SEQ ID NO: 2 with C in $15^{th}$ position of SEQ ID NO: 1 and AU in $3^{rd}$ and $4^{th}$ positions of SEQ ID NO: 2 respectively forming an internal loop. Circled is the methylatable adenine.

Example 4: Identification of Methylation Activity for Substrates Made of Two Polynucleotides In order to more clearly specify the minimum substrate of 23S rRNA that can be methylated by the Erm protein, a construct in which two polynucleotide strands consisting of part of the original Helix 73 sequence without artificial nucleotides are annealed was prepared, and the substrate activity thereof for ErmS was examined. The construct was a combination of the first nucleotide consisting of the sequence of SEQ ID NO: 9 (AGGACGGA) and the second nucleotide consisting of the sequence of SEQ ID NO: 10 (CCUAUCC), and was named 15nt RNA (see FIG. 10).

Following annealing the first nucleotide and the second nucleotide at 10° C., the methylation activity was examined with increase in the incubation temperature. The construct did not exhibit any methylation activity at 37° C. and room temperature, even after incubation for 15 hours. It was considered that the construct failed to maintain a duplex state in which the two strands are complementarily paired due to a high temperature.

Figure 9:
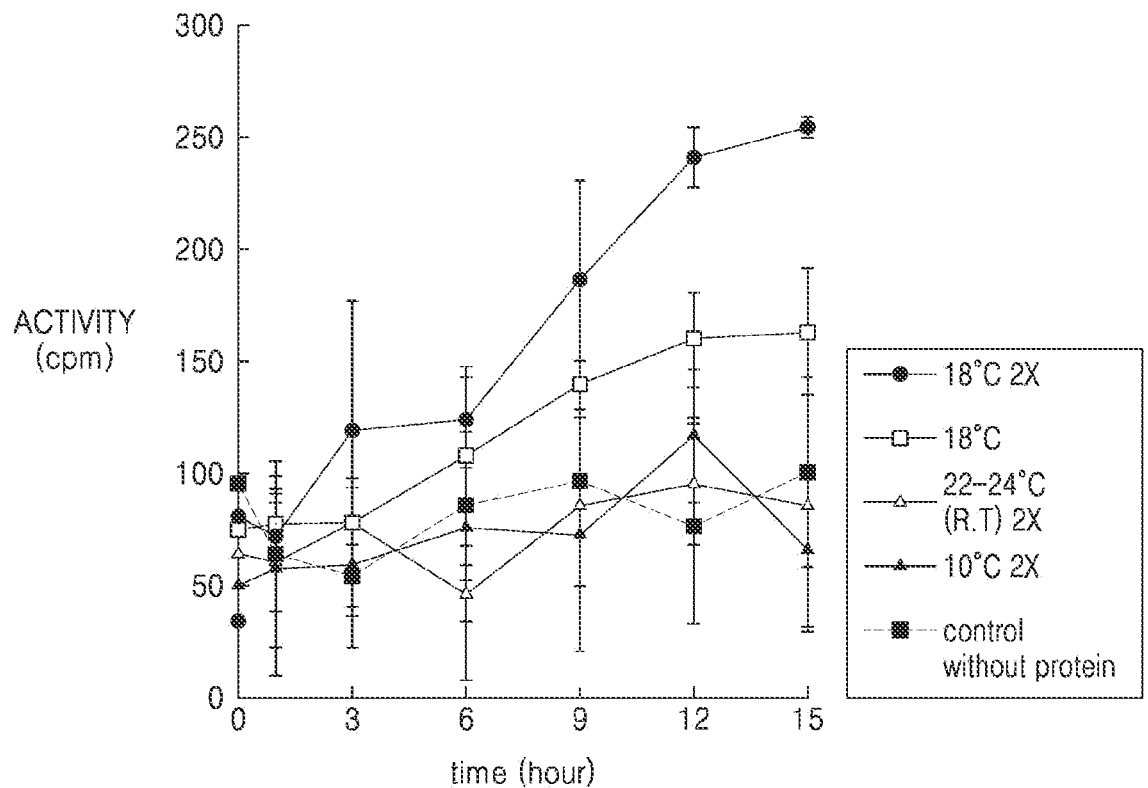
FIG. 9 shows the activity of ErmS for 15 nt.

According to FIG. 9, when the incubation temperature was 18° C., the construct became a duplex to exhibit methylation activity. However, if the incubation temperature was lowered to the minimum annealing temperature of 10° C., methylation activity was not shown. Accordingly, the optimum temperature for enzymatic activity of Erm may be 10° C. or higher.

In order to identify the methylation activity of ErmS for the construct, the amounts of substrate, Erm enzyme, and methyl donor (SAM) required for the reaction were doubled and the methylation activity was determined. Reaction condition was set to be 18° C. for 12 hours.

According to Table 6 and FIG. 9, 15nt exhibited methylation activity by EmrS, and the degree of methylation activity confirmed was similar to that of ErmE for 567nt.

TABLE 5

| RNA | ErmS | ErmB | ErmE | Control, 24nt without protein |
|---|---|---|---|---|
| 24nt | + | + | + | − |
| 23nt | + | − | − | − |
| 22nt | + | ND | ND | − |
| 21nt | + | ND | ND | − |
| 20nt-ll | + | ND | ND | − |

TABLE 6

| RNA substrate | ErmS | ErmB | ErmE | Control without protein |
|---|---|---|---|---|
| 24nt | + | + | + | − |
| 24nt A2058G | − | − | − | − |
| 24nt A2058C | − | − | − | − |
| 24nt A2058U | − | − | − | − |
| g21nt | + | − | − | − |
| g21nt A2058G | − | ND (not determine) | ND | ND |

TABLE 6-continued

| RNA substrate | ErmS | ErmB | ErmE | Control without protein |
|---|---|---|---|---|
| g21nt A2058C | − | ND | ND | ND |
| g21nt A2058U | − | ND | ND | ND |
| 20nt-ll | + | ND | ND | − |
| 20nt-ll A2058G | − | ND | ND | ND |
| 20nt-ll A2058C | − | ND | ND | ND |
| 20nt-ll A2058U | − | ND | ND | ND |
| Annealed 15nt | + (18° C.) | ND | ND | − |
| Annealed 15nt A2058C | − (18° C.) | ND | ND | ND |
| Annealed 15nt A2058U | − (18° C.) | ND | ND | ND |

Although not shown in the table, the substitution of A2058 in 15nt with C or U confirmed the methylation site to be A2058 as in the above experiment.

The double-stranded RNA molecule of the present invention can also be used to improve antibiotic resistance expression inhibitors. Specifically, an inhibitor that binds to a specific site among the first to third Erm interaction sites may be modified to further increase a binding strength thereof, or may be modified to interact with sites other than the original binding site. For example, the double-stranded RNA molecule of the present invention can be used to develop an inhibitor having an increased antibiotic resistance expression inhibitory effect, for example by modifying an inhibitor acting on the first Erm interaction site to further increase the interaction, or by modifying the same to interact with the second Erm interaction site in addition to the first Erm interaction site. In another example, an inhibitor acting on the second Erm interaction site may be modified to further increase the interaction thereof, or may be modified to interact with one or more of the first Erm interaction site and the third Erm interaction site. In another example, an inhibitor acting on a third Erm interaction site may be modified to further increase the interaction thereof, or may be modified to interact with one or more of the first Erm interaction site and the second Erm interaction site. In another example, an inhibitor acting on a minimum substrate site may be modified to further increase the interaction thereof, or may be modified to interact with at least one of the second Erm interaction site and the third Erm interaction site. In addition, an inhibitor acting on the third Erm interaction site may be modified to further increase the interaction thereof, or may be modified to interact further with the minimum substrate site.

The double-stranded RNA molecule of the present invention can be used to inhibit the expression of antibiotic resistance by an Erm protein.

In addition, the double-stranded RNA molecule of the present invention can also be used to determine a structure of a complex in which an Erm protein and an RNA are bound. In view of the above, an inhibitor that mimics the structure of an RNA alone or that combined with Erm protein as obtained above may be developed A novel antibiotic resistance expression inhibitor may be obtained through a method for screening an antibiotic resistance expression inhibitor by using a double-stranded RNA molecule or a variant thereof according to an embodiment of the present invention, or modification or improvement of existing inhibitors may be pursued in a reasonable manner.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method for screening an antibiotic resistance expression inhibitor, comprising the steps of:
contacting a double-stranded RNA molecule or a variant thereof with an Erm protein and a candidate substance, wherein the double-stranded RNA molecule or variant thereof is a substrate for methylation by the Erm protein, and the antibiotic is a macrolide-lincosamide-streptogramin B (MLSB) class antibiotic; and
identifying whether the candidate substance inhibits the methylation by the Erm protein, wherein if the candidate substance inhibits the methylation, the candidate substance is selected as an antibiotic resistance expression inhibitor which inhibits expression of antibiotic resistance by inhibiting methylation by the Erm protein, thereby rendering microorganism expressing Erm protein sensitive to antibiotics,
wherein the double-stranded RNA molecule or variant thereof is a double-stranded RNA molecule in which:
a first strand consisting of the sequence of SEQ ID NO: 1 and a second strand consisting of the sequence of SEQ ID NO: 2 are paired while forming 13 base pairs,
the first and second bases of SEQ ID NO: 1 form a 5' overhang,
the 19th to 22nd bases of SEQ ID NO: 1 form a 3' overhang,
the 11th base of SEQ ID NO: 1 is an unpaired base,
the 15th base of SEQ ID NO: 1 and the 3rd and 4th bases of SEQ ID NO: 2 forms an internal loop, and
the $18^{th}$ base of SEQ ID NO: 1 is adenine to be methylated by an Erm protein, and
wherein the variant comprises one of the following mutations in the double-stranded RNA molecule:
deletion of all or part of 5' overhang of the first strand;
truncation of all or part of base pairs between the 5' end of the first strand and the 11th unpaired base of SEQ ID NO: 1;
truncation of all or part of base pairs between the 5' end of the first strand and the 11th unpaired base of SEQ ID NO: 1 and deletion of the first and second bases of SEQ ID NO: 1;
truncation of all or part of base pairs between the 5' end of the first strand and the 11th unpaired base of SEQ ID NO: 1 and addition of a tetraloop sequence to cap the remaining end of the base pairs after truncation;
truncation of all or part of base pairs between the 5' end of the first strand and the 11th unpaired base of SEQ ID NO: 1, addition of a tetraloop sequence to the side of the truncation, and deletion of the first and second bases of SEQ ID NO: 1;
truncation of none or all or part of base pairs between the 5' end of the first strand and the 11th unpaired base of SEQ ID NO: 1 and $11^{th}$ unpaired base, addition of a tetraloop sequence to the side of the truncation;
addition of a tetraloop sequence to all of base pairs between the 5' end of the first strand and the 11th unpaired base of SEQ ID NO: 1;
addition of a tetraloop sequence to all or part or none of base pairs between the 5' end of the first strand and the 11th unpaired base of SEQ ID NO: 1 and truncation of the 11th unpaired base, and deletion of the first and second bases of SEQ ID NO: 1;
deletion of the $19^{th}$ to 22nd bases or part thereof in the 3' overhang of the first strand;
truncation of all or part of base pairs between the 5' end of the first strand and the 11th unpaired base of SEQ ID NO: 1 and addition of a hairpin loop formed by linking the 3' overhang of the first strand to the 5' end of the second strand via the extra CC added; and
deletion of 5'-overhang of the first strand, truncation of all or part of base pairs between the 5' end of the first strand and the 11th unpaired base of SEQ ID NO: 1 and addition of a hairpin loop formed by linking the 3' overhang of the first strand to the 5' end of the second strand via the extra CC added.

2. The method of claim 1, wherein the contacting step includes contacting a double-stranded RNA molecule or a variant thereof and a candidate substance; and adding an Erm protein to the double-stranded RNA molecule or a variant thereof and the candidate substance; or contacting an Erm protein and a candidate substance and adding a double-stranded RNA molecule or a variant thereof to the Erm protein and the candidate substance; or contacting an Erm protein and a double-stranded RNA molecule or a variant thereof; and adding an candidate substance to the Erm protein and the double-stranded RNA molecule or the variant thereof.

3. The method of claim 1, wherein the inhibition of methylation includes inhibiting the methylation through the interaction of the double-stranded RNA molecule or a variant thereof with inhibitor and/or the Erm protein with inhibitor and/or inhibition of interaction of the Erm protein with the double-stranded RNA molecule and/or the activity of complex between the Erm protein and the double-stranded RNA molecule or a variant thereof.

4. The method of claim 1, wherein the antibiotic resistance expression inhibitor inhibits the antibiotic resistance of bacteria belonging to Firmicutes, *Bacteroides*, Proteobacteria and Actinobacteria.

5. The method of claim 3, wherein the double-stranded RNA molecule or the variant thereof inhibits the interaction between Erm protein and substrate RNA and is selected from the following:
(a) a double-stranded RNA molecule consisting of 3 base pairs in which the sequence of SEQ ID NO: 6 and a sequence complementary thereto are paired, or part thereof,
(b) a double-stranded RNA molecule consisting of 5 base pairs in which the sequence of SEQ ID NO: 7 and a sequence complementary thereto are paired, or part thereof,
(c) a double-stranded RNA molecule consisting of 8 base pairs in which the sequence of SEQ ID NO: 8 and a sequence complementary thereto are paired, or part thereof,
(d) a double-stranded RNA molecule in which the sequence of SEQ ID NO: 9 and the sequence of SEQ ID NO: 10 are paired or a variant thereof in which a portion of the double-stranded RNA molecule is deleted;
(e) a single-stranded RNA molecule consisting of a sequence of SEQ ID NO: 5 in which the 6th and 7th bases are removed, or a partial sequence thereof,
(f) a double-stranded RNA molecule variant in which the sequence of SEQ ID NO: 11 and the sequence of SEQ ID NO: 12 are paired, or a variant thereof in which a portion of the double-stranded RNA molecule is deleted;
(g) a double-stranded RNA molecule in which the sequence of SEQ ID NO: 13 and the sequence of SEQ ID NO: 14 are paired, or a variant thereof in which a portion of the double-stranded RNA molecule is deleted;

(h) a double-stranded RNA molecule in which the sequence of SEQ ID NO: 1 and the sequence of SEQ ID NO: 2 are paired, or a variant thereof in which a portion of the double-stranded RNA molecule is deleted;

(i) a double-stranded RNA molecule in which the sequence of SEQ ID NO: 15 and the sequence of SEQ ID NO: 16 are paired, or a variant thereof in which a portion of the double-stranded RNA molecule is deleted; and (j) a double-stranded RNA molecule in which the sequence of SEQ ID NO: 17 and the sequence of SEQ ID NO: 18 are paired, or a variant thereof in which a portion of the double-stranded RNA molecule is deleted.

6. The method of claim 1, wherein the double-stranded RNA molecule consists of the sequence of SEQ ID NO: 61, and has a stem structure comprising 13 base pairs in which part of 15 consecutive bases at the 5' end region of SEQ ID NO: 61 and part of 15 consecutive bases at the 3' end region thereof are complementarily paired, wherein the ninth base of SEQ ID NO: 61 is an unpaired base and the $13^{th}$ base of SEQ ID NO:61 and two bases UA in the opposite strand forms internal loop.

7. The method of claim 1, wherein the double-stranded RNA molecule consists of the sequence of SEQ ID NO: 61, and has a stem structure comprising 13 base pairs in which part of 15 consecutive bases at the 5' end region of SEQ ID NO: 61 and part of 15 consecutive bases at the 3' end region thereof are complementarily paired, wherein the ninth base of SEQ ID NO: 61 is an unpaired base, and a variant of the double-stranded RNA molecule consists of the sequence of SEQ ID NO: 61 in which all or part of 1 to 8 base pairs located between the end of the stem structure and the ninth base of SEQ ID NO: 61 are truncated.

8. The method of claim 1, wherein the Erm is at least one selected from the group consisting of ErmB, ErmE, and ErmS.

* * * * *

SEQUENCE LISTING

```
<160> NUMBER OF SEQ ID NOS: 63

<210> SEQ ID NO 1
<211> LENGTH: 22
<212> TYPE: RNA
<213> ORGANISM: Artificial
<220> FEATURE:
<223> OTHER INFORMATION: gg583nt sense strand

<400> SEQUENCE: 1
ggcccgcgac aggacggaaa ga                                    22

<210> SEQ ID NO 2
<211> LENGTH: 15
<212> TYPE: RNA
<213> ORGANISM: Artificial
<220> FEATURE:
<223> OTHER INFORMATION: gg583nt antisense strand

<400> SEQUENCE: 2
ccuauccguc gcggg                                            15

<210> SEQ ID NO 3
<211> LENGTH: 4
<212> TYPE: RNA
<213> ORGANISM: Artificial
```

```
<220> FEATURE:
<223> OTHER INFORMATION: tetra loop

<400> SEQUENCE: 3 uucg                                                                    4

<210> SEQ ID NO 4
<211> LENGTH: 4
<212> TYPE: RNA
<213> ORGANISM: Artificial
<220> FEATURE:
<223> OTHER INFORMATION: tetra loop

<400> SEQUENCE: 4 gcaa                                                                    4

<210> SEQ ID NO 5
<211> LENGTH: 7
<212> TYPE: RNA
<213> ORGANISM: Artificial
<220> FEATURE:
<223> OTHER INFORMATION: hairpin loop

<400> SEQUENCE: 5 aaagacc                                                                 7

<210> SEQ ID NO 6
<211> LENGTH: 3
<212> TYPE: RNA
<213> ORGANISM: Artificial
<220> FEATURE:
<223> OTHER INFORMATION: 1 Erm interaction region

<400> SEQUENCE: 6 ccc                                                                     3

<210> SEQ ID NO 7
<211> LENGTH: 5
<212> TYPE: RNA
<213> ORGANISM: Artificial
<220> FEATURE:
<223> OTHER INFORMATION: 2 Erm interaction region

<400> SEQUENCE: 7 gcgac                                                                   5

<210> SEQ ID NO 8
<211> LENGTH: 8
<212> TYPE: RNA
<213> ORGANISM: Artificial
<220> FEATURE:
<223> OTHER INFORMATION: 1 Erm interaction region and 2 Erm interaction
      region

<400> SEQUENCE: 8 cccgcgac                                                                8

<210> SEQ ID NO 9
<211> LENGTH: 8
<212> TYPE: RNA
<213> ORGANISM: Artificial
<220> FEATURE:
<223> OTHER INFORMATION: minimal substrate sense strand

<400> SEQUENCE: 9 aggacgga                                                                8
```

```
<210> SEQ ID NO 10
<211> LENGTH: 7
<212> TYPE: RNA
<213> ORGANISM: Artificial
<220> FEATURE:
<223> OTHER INFORMATION: minimal substrate antisense strand

<400> SEQUENCE: 10 ccuaucc                                                                       7

<210> SEQ ID NO 11
<211> LENGTH: 13
<212> TYPE: RNA
<213> ORGANISM: Artificial
<220> FEATURE:
<223> OTHER INFORMATION: 2 Erm interaction region and minimal substrate
      sense sequence

<400> SEQUENCE: 11
gcgacaggac gga                                                               13

<210> SEQ ID NO 12
<211> LENGTH: 12
<212> TYPE: RNA
<213> ORGANISM: Artificial
<220> FEATURE:
<223> OTHER INFORMATION: 2 Erm interaction region and minimal substrate
      antisense sequence

<400> SEQUENCE: 12
ccuauccguc gc                                                                12

<210> SEQ ID NO 13
<211> LENGTH: 12
<212> TYPE: RNA
<213> ORGANISM: Artificial
<220> FEATURE:
<223> OTHER INFORMATION: 3 Erm interaction region and minimal substrate
      sense sequence

<400> SEQUENCE: 13
aggacggaaa ga                                                                12

<210> SEQ ID NO 14
<211> LENGTH: 7
<212> TYPE: RNA
<213> ORGANISM: Artificial
<220> FEATURE:
<223> OTHER INFORMATION: 3 Erm interaction region and minimal substrate
      antisense sequence

<400> SEQUENCE: 14 ccuaucc                                                                       7

<210> SEQ ID NO 15
<211> LENGTH: 16
<212> TYPE: RNA
<213> ORGANISM: Artificial
<220> FEATURE:
<223> OTHER INFORMATION: 1 Erm interaction region + 2 Erm interaction
      region + minimal substrate sense seq

<400> SEQUENCE: 15
cccgcgacag gacgga                                                            16
```

```
<210> SEQ ID NO 16
<211> LENGTH: 15
<212> TYPE: RNA
<213> ORGANISM: Artificial
<220> FEATURE:
<223> OTHER INFORMATION: 1 Erm interaction region + 2 Erm interaction
      region + minimal substrate antisense seq

<400> SEQUENCE: 16
ccuauccguc gcggg                                                          15

<210> SEQ ID NO 17
<211> LENGTH: 17
<212> TYPE: RNA
<213> ORGANISM: Artificial
<220> FEATURE:
<223> OTHER INFORMATION: 2 Erm interaction region + minimal substrate +
      3 Erm interaction region sense seq

<400> SEQUENCE: 17
gcgacaggac ggaaaga                                                        17

<210> SEQ ID NO 18
<211> LENGTH: 12
<212> TYPE: RNA
<213> ORGANISM: Artificial
<220> FEATURE:
<223> OTHER INFORMATION: 2 Erm interaction region + minimal substrate +
      3 Erm interaction region antisense seq

<400> SEQUENCE: 18
ccuauccguc gc                                                             12

<210> SEQ ID NO 19
<211> LENGTH: 52
<212> TYPE: DNA
<213> ORGANISM: Artificial
<220> FEATURE:
<223> OTHER INFORMATION: F primer for ErmB expression vector

<400> SEQUENCE: 19
ggaattccat atgaacaaaa acatcaaata ctctcaaaac tttttaacga at                 52

<210> SEQ ID NO 20
<211> LENGTH: 30
<212> TYPE: DNA
<213> ORGANISM: Artificial
<220> FEATURE:
<223> OTHER INFORMATION: R primer for ErmB expression vector

<400> SEQUENCE: 20
ccgctcgagt ttcctcccgt taaataatag                                          30

<210> SEQ ID NO 21
<211> LENGTH: 25
<212> TYPE: DNA
<213> ORGANISM: Artificial
<220> FEATURE:
<223> OTHER INFORMATION: Oligo 1

<400> SEQUENCE: 21
ggaattctaa tacgactcac tatag                                               25

<210> SEQ ID NO 22
<211> LENGTH: 24
<212> TYPE: DNA
<213> ORGANISM: Artificial
```

```
<220> FEATURE:
<223> OTHER INFORMATION: Oligo 1-1

<400> SEQUENCE: 22
ggaattctaa tacgactcac tata                                              24

<210> SEQ ID NO 23
<211> LENGTH: 35
<212> TYPE: DNA
<213> ORGANISM: Artificial
<220> FEATURE:
<223> OTHER INFORMATION: Oligo 2

<400> SEQUENCE: 23
cgactcacta taggcccgcg acaggacgga aagac                                  35

<210> SEQ ID NO 24
<211> LENGTH: 35
<212> TYPE: DNA
<213> ORGANISM: Artificial
<220> FEATURE:
<223> OTHER INFORMATION: Oligo 2-1

<400> SEQUENCE: 24
cgactcacta taggcccgcg acaggacggg aagac                                  35

<210> SEQ ID NO 25
<211> LENGTH: 35
<212> TYPE: DNA
<213> ORGANISM: Artificial
<220> FEATURE:
<223> OTHER INFORMATION: Oligo 2-2

<400> SEQUENCE: 25
cgactcacta taggcccgcg acaggacggc aagac                                  35

<210> SEQ ID NO 26
<211> LENGTH: 35
<212> TYPE: DNA
<213> ORGANISM: Artificial
<220> FEATURE:
<223> OTHER INFORMATION: Oligo 2-3

<400> SEQUENCE: 26
cgactcacta taggcccgcg acaggacggt aagac                                  35

<210> SEQ ID NO 27
<211> LENGTH: 35
<212> TYPE: DNA
<213> ORGANISM: Artificial
<220> FEATURE:
<223> OTHER INFORMATION: Oligo 3

<400> SEQUENCE: 27
gggaccatgg ccggccccgc gacggatagg gaccg                                  35

<210> SEQ ID NO 28
<211> LENGTH: 57
<212> TYPE: DNA
<213> ORGANISM: Artificial
<220> FEATURE:
<223> OTHER INFORMATION: Oligo 4

<400> SEQUENCE: 28
gtcccctcgg aatgttgccc accggccgcc agcgaggagg ctgggaccat ggccggc          57
```

<210> SEQ ID NO 29
<211> LENGTH: 49
<212> TYPE: DNA
<213> ORGANISM: Artificial
<220> FEATURE:
<223> OTHER INFORMATION: Oligo 5

<400> SEQUENCE: 29
gctctagagt cccattcgcc attaccgagg ggacggtccc ctcggaatg                49

<210> SEQ ID NO 30
<211> LENGTH: 33
<212> TYPE: DNA
<213> ORGANISM: Artificial
<220> FEATURE:
<223> OTHER INFORMATION: Oligo 6

<400> SEQUENCE: 30
cgactcacta tagcgacagg acggaaagac ccc                                 33

<210> SEQ ID NO 31
<211> LENGTH: 35
<212> TYPE: DNA
<213> ORGANISM: Artificial
<220> FEATURE:
<223> OTHER INFORMATION: Oligo 7

<400> SEQUENCE: 31
gggaccatgg ccggcgcgac ggatagggac cgaac                               35

<210> SEQ ID NO 32
<211> LENGTH: 32
<212> TYPE: DNA
<213> ORGANISM: Artificial
<220> FEATURE:
<223> OTHER INFORMATION: Oligo 8

<400> SEQUENCE: 32
cgactcacta taaggacgga aagacccgt gg                                   32

<210> SEQ ID NO 33
<211> LENGTH: 32
<212> TYPE: DNA
<213> ORGANISM: Artificial
<220> FEATURE:
<223> OTHER INFORMATION: Oligo 8-1

<400> SEQUENCE: 33
cgactcacta taaggacggg aagacccgt gg                                   32

<210> SEQ ID NO 34
<211> LENGTH: 32
<212> TYPE: DNA
<213> ORGANISM: Artificial
<220> FEATURE:
<223> OTHER INFORMATION: Oligo 8-2

<400> SEQUENCE: 34
cgactcacta taaggacggc aagacccgt gg                                   32

<210> SEQ ID NO 35
<211> LENGTH: 32
<212> TYPE: DNA
<213> ORGANISM: Artificial
<220> FEATURE:
<223> OTHER INFORMATION: Oligo 8-3

```
<400> SEQUENCE: 35
cgactcacta taaggacggt aagaccccgt gg                              32

<210> SEQ ID NO 36
<211> LENGTH: 32
<212> TYPE: DNA
<213> ORGANISM: Artificial
<220> FEATURE:
<223> OTHER INFORMATION: Oligo 8-4

<400> SEQUENCE: 36
cgactcacta tacggacgga aagaccccgt gg                              32

<210> SEQ ID NO 37
<211> LENGTH: 32
<212> TYPE: DNA
<213> ORGANISM: Artificial
<220> FEATURE:
<223> OTHER INFORMATION: Oligo 8-5

<400> SEQUENCE: 37
cgactcacta tatggacgga aagaccccgt gg                              32

<210> SEQ ID NO 38
<211> LENGTH: 33
<212> TYPE: DNA
<213> ORGANISM: Artificial
<220> FEATURE:
<223> OTHER INFORMATION: Oligo 9

<400> SEQUENCE: 38
cgactcacta taggacggaa agaccccgtg gag                             33

<210> SEQ ID NO 39
<211> LENGTH: 30
<212> TYPE: DNA
<213> ORGANISM: Artificial
<220> FEATURE:
<223> OTHER INFORMATION: Oligo 10

<400> SEQUENCE: 39
gggaccatgg ccggcggata gggaccgaac                                 30

<210> SEQ ID NO 40
<211> LENGTH: 49
<212> TYPE: DNA
<213> ORGANISM: Artificial
<220> FEATURE:
<223> OTHER INFORMATION: Oligo 11

<400> SEQUENCE: 40
cgactcacta taggcccgcg acaggacgga aagacccta tccgtcgcg             49

<210> SEQ ID NO 41
<211> LENGTH: 40
<212> TYPE: DNA
<213> ORGANISM: Artificial
<220> FEATURE:
<223> OTHER INFORMATION: Oligo 12

<400> SEQUENCE: 41
gggaccatgg ccggccccgc gacggatagg ggtctttccg                      40

<210> SEQ ID NO 42
```

```
<211> LENGTH: 49
<212> TYPE: DNA
<213> ORGANISM: Artificial
<220> FEATURE:
<223> OTHER INFORMATION: Oligo 13

<400> SEQUENCE: 42
cgactcacta tagaggacgg aaagacccct atccgccggc catggtccc            49

<210> SEQ ID NO 43
<211> LENGTH: 49
<212> TYPE: DNA
<213> ORGANISM: Artificial
<220> FEATURE:
<223> OTHER INFORMATION: Oligo 13-1

<400> SEQUENCE: 43
cgactcacta tagaggacgg gaagacccct atccgccggc catggtccc            49

<210> SEQ ID NO 44
<211> LENGTH: 49
<212> TYPE: DNA
<213> ORGANISM: Artificial
<220> FEATURE:
<223> OTHER INFORMATION: Oligo 13-2

<400> SEQUENCE: 44
cgactcacta tagaggacgg caagacccct atccgccggc catggtccc            49

<210> SEQ ID NO 45
<211> LENGTH: 49
<212> TYPE: DNA
<213> ORGANISM: Artificial
<220> FEATURE:
<223> OTHER INFORMATION: Oligo 13-3

<400> SEQUENCE: 45
cgactcacta tagaggacgg taagacccct atccgccggc catggtccc            49

<210> SEQ ID NO 46
<211> LENGTH: 49
<212> TYPE: DNA
<213> ORGANISM: Artificial
<220> FEATURE:
<223> OTHER INFORMATION: Oligo 13-4

<400> SEQUENCE: 46
cgactcacta tagcggacgg aaagacccct atccgccggc catggtccc            49

<210> SEQ ID NO 47
<211> LENGTH: 49
<212> TYPE: DNA
<213> ORGANISM: Artificial
<220> FEATURE:
<223> OTHER INFORMATION: Oligo 13-5

<400> SEQUENCE: 47
cgactcacta tagtggacgg aaagacccct atccgccggc catggtccc            49

<210> SEQ ID NO 48
<211> LENGTH: 47
<212> TYPE: DNA
<213> ORGANISM: Artificial
<220> FEATURE:
<223> OTHER INFORMATION: Oligo 14

<400> SEQUENCE: 48
```
cgactcacta taggacggaa agaccctat ccgccggcca tggtccc        47

<210> SEQ ID NO 49
<211> LENGTH: 51
<212> TYPE: DNA
<213> ORGANISM: Artificial
<220> FEATURE:
<223> OTHER INFORMATION: Oligo 15

<400> SEQUENCE: 49
cgactcacta taggcctatc cttcgggacg aaagagccg gccatggtcc c        51

<210> SEQ ID NO 50
<211> LENGTH: 51
<212> TYPE: DNA
<213> ORGANISM: Artificial
<220> FEATURE:
<223> OTHER INFORMATION: Oligo 15-1

<400> SEQUENCE: 50
cgactcacta taggcctatc cttcgggacg ggaagagccg gccatggtcc c        51

<210> SEQ ID NO 51
<211> LENGTH: 51
<212> TYPE: DNA
<213> ORGANISM: Artificial
<220> FEATURE:
<223> OTHER INFORMATION: Oligo 15-2

<400> SEQUENCE: 51
cgactcacta taggcctatc cttcgggacg gcaagagccg gccatggtcc c        51

<210> SEQ ID NO 52
<211> LENGTH: 51
<212> TYPE: DNA
<213> ORGANISM: Artificial
<220> FEATURE:
<223> OTHER INFORMATION: Oligo 15-3

<400> SEQUENCE: 52
cgactcacta taggcctatc cttcgggacg gtaagagccg gccatggtcc c        51

<210> SEQ ID NO 53
<211> LENGTH: 49
<212> TYPE: DNA
<213> ORGANISM: Artificial
<220> FEATURE:
<223> OTHER INFORMATION: Oligo 16

<400> SEQUENCE: 53
cgactcacta taggcctatc ttcggacgga aagagccggc catggtccc        49

<210> SEQ ID NO 54
<211> LENGTH: 50
<212> TYPE: DNA
<213> ORGANISM: Artificial
<220> FEATURE:
<223> OTHER INFORMATION: Oligo 17

<400> SEQUENCE: 54
cgactcacta taggcctatc cttcgggacg gaaaggccgg ccatggtccc        50

<210> SEQ ID NO 55
<211> LENGTH: 49
<212> TYPE: DNA

```
<213> ORGANISM: Artificial
<220> FEATURE:
<223> OTHER INFORMATION: Oligo 18

<400> SEQUENCE: 55
cgactcacta taggcctatc cttcgggacg aaagccggc catggtccc          49

<210> SEQ ID NO 56
<211> LENGTH: 48
<212> TYPE: DNA
<213> ORGANISM: Artificial
<220> FEATURE:
<223> OTHER INFORMATION: Oligo 19

<400> SEQUENCE: 56
cgactcacta taggcctatc cttcgggacg aagccggcc atggtccc           48

<210> SEQ ID NO 57
<211> LENGTH: 47
<212> TYPE: DNA
<213> ORGANISM: Artificial
<220> FEATURE:
<223> OTHER INFORMATION: Oligo 20

<400> SEQUENCE: 57
cgactcacta taggcctatc cttcgggacg gagccggcca tggtccc           47

<210> SEQ ID NO 58
<211> LENGTH: 46
<212> TYPE: DNA
<213> ORGANISM: Artificial
<220> FEATURE:
<223> OTHER INFORMATION: Oligo 20-1

<400> SEQUENCE: 58
cgactcacta taggcctatc cttcgggacg gggccggcca tggtcc            46

<210> SEQ ID NO 59
<211> LENGTH: 46
<212> TYPE: DNA
<213> ORGANISM: Artificial
<220> FEATURE:
<223> OTHER INFORMATION: Oligo 20-2

<400> SEQUENCE: 59
cgactcacta taggcctatc cttcgggacg gcgccggcca tggtcc            46

<210> SEQ ID NO 60
<211> LENGTH: 46
<212> TYPE: DNA
<213> ORGANISM: Artificial
<220> FEATURE:
<223> OTHER INFORMATION: Oligo 20-3

<400> SEQUENCE: 60
cgactcacta taggcctatc cttcgggacg gtgccggcca tggtcc            46

<210> SEQ ID NO 61
<211> LENGTH: 583
<212> TYPE: RNA
<213> ORGANISM: Artificial
<220> FEATURE:
<223> OTHER INFORMATION: 23S rRNA Domain V fragment - 583nt

<400> SEQUENCE: 61
cccgcgacag gacggaaaga ccccguggag cuuuacugca gccugauauu gaauguuggu    60
```

```
acagcuugua caggauaggu aggagccuug gaaaccggag cgccagcuuc ggugaggca      120 ucgguggau  acuacccugg cuguauugac cuucuaaccc gccgcccuua ucgggcgggg     180
agacagaguc agguggcag  uuugacuggg gcggucgccu ccuaaaaggu aacggaggcg     240
cccaaagguu cccucagaau gguuggaaau cauucgcaga guguaaaggc acaagggagc     300
uugacugcga gaccuacaag ucgagcaggg acgaaagucg gcuuaguga uccggugguu     360 ccgcauggaa gggccaucgc ucaacggaua aaagcuaccc ggggauaaac aggcuuaucu     420
cccccaagag uccacaucga cggggagguu uggcaccucg augucggcuc aucgcauccu    480
ggggcuguag ucguucccaa gguugggcu  guucgcccau uaaagcggua cgcgagcugg    540
guucagaacg ucgugagaca guucggucc  uauccgucgc ggg                      583

<210> SEQ ID NO 62
<211> LENGTH: 577
<212> TYPE: RNA
<213> ORGANISM: Artificial
<220> FEATURE:
<223> OTHER INFORMATION: 577nt

<400> SEQUENCE: 62
gcgacaggac ggaaagaccc cguggagcuu acugcagcc  ugauauugaa uguugguaca      60
gcuuguacag gauagguagg agccuuggaa accggagcgc cagcuucggu ggaggcaucg     120
gugggauacu acccuggcug uauugaccuu cuaacccgcc gcccuaucg  ggcggggaga    180 cagugucagg uggcaguuu  gacugggcg  gucgccuccu aaaagguaac ggaggcgccc    240
aagguucccc ucagaauggu uggaaaucau ucgcagagug uaaaggcaca agggagcuug    300
acugcgagac cuacaagucg agcagggacg aaagucgggc uuagauccc ggugguuccg    360 cauggaaggg ccaucgcuca acggauaaaa gcuacccggg gauaacagg  cuuaucuccc    420 ccaagaagucc acaucgacgg ggagguuugg caccucgaug ucggcucauc gcauccuggg   480 gcuguagcg  gucccaaggg uugggcuguu cgcccauuaa agcggacgc  gagcugggu u  540 cagaacgucg ugagacaguu cggucccuau ccgucgc                             577

<210> SEQ ID NO 63
<211> LENGTH: 567
<212> TYPE: RNA
<213> ORGANISM: Artificial
<220> FEATURE:
<223> OTHER INFORMATION: 567nt

<400> SEQUENCE: 63
aggacggaaa gaccccgugg agcuuuacug cagccugaua uugaauguug uacagcuug      60 uacaggauag guaggagccu ggaaaccgg  agcgccagcu ucgguggagg caucgguggg    120
auacuacccu ggcuguauug accuucuaac ccgccgcccu uaucgggcgg ggagacagug    180
ucaggugggc aguuugacug ggcggucgc  ucccuaaaag guaacggagg cgcccaaagg    240 uuccccucaga augguuggaa ucauucgca  gagaguaaag gcacaaggga gcuugacugc    300
gagaccuaca agucgagcag ggacgaaagu cgggcuuagu gauccggugg uuccgcaugg    360
aagggccauc gcucaacgga uaaaagcuac cccggggaua acaggcuuau cucccccaag    420
aguccacauc gacggggagg uuuggcaccu cgaucggc  ucaucgcauc cugggggcugu    480 agucggucc  aaggguuggg cuguucgcc  auuaaagcgg uacgcgagcu ggguucagaa    540
cgucgugaga caguucgguc ccuaucc                                        567
```